US008563290B2

(12) United States Patent
Glad et al.

(10) Patent No.: US 8,563,290 B2
(45) Date of Patent: *Oct. 22, 2013

(54) PECTATE LYASE VARIANTS

(75) Inventors: Sanne Schroder Glad, Ballerup (DK); Carsten Andersen, Vaerloese (DK); Torben Vedel Borchert, Birkerod (DK); Katja Salomon Johansen, Gentofte (DK); Henrik Frisner, Copenhagen (DK); Mads Eskelund Bjornvad, Frederiksberg (DK); Thomas Thisted, Frederikssund (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/605,455

(22) Filed: Sep. 6, 2012

(65) Prior Publication Data

US 2013/0012424 A1    Jan. 10, 2013

Related U.S. Application Data

(62) Division of application No. 12/481,922, filed on Jun. 10, 2009, now Pat. No. 8,288,144, which is a division of application No. 10/513,951, filed as application No. PCT/DK03/00316 on May 14, 2003, now Pat. No. 7,601,529.

(60) Provisional application No. 60/381,182, filed on May 18, 2002.

(30) Foreign Application Priority Data

May 14, 2002 (DK) .................................. 2002 00746

(51) Int. Cl.
| C12N 9/88 | (2006.01) |
| C11D 3/386 | (2006.01) |
| D06M 16/00 | (2006.01) |
| C12N 15/74 | (2006.01) |
| C12N 15/75 | (2006.01) |
| C12N 15/79 | (2006.01) |

(52) U.S. Cl.
USPC .. 435/232; 435/69.1; 435/252.3; 435/254.11; 435/320.1; 435/263; 435/264; 510/226; 510/300; 510/392; 536/23.2

(58) Field of Classification Search
None
See application file for complete search history.

(56) References Cited

U.S. PATENT DOCUMENTS

| 6,124,127 | A  | 9/2000  | Andersen et al. |
| 6,165,769 | A  | 12/2000 | Andersen et al. |
| 6,172,030 | B1 | 1/2001  | Wada et al. |
| 6,187,580 | B1 | 2/2001  | Andersen et al. |
| 6,242,014 | B1 | 6/2001  | Xu |
| 6,258,590 | B1 | 7/2001  | Lange et al. |
| 6,280,995 | B1 | 8/2001  | Andersen et al. |
| 6,284,524 | B1 | 9/2001  | Andersen et al. |
| 6,368,843 | B1 | 4/2002  | Andersen et al. |
| 6,399,351 | B1 | 6/2002  | Bjornvad et al. |
| 6,429,000 | B1 | 8/2002  | Andersen et al. |
| 6,607,902 | B2 | 8/2003  | Glad et al. |
| 6,630,342 | B2 | 10/2003 | Lange et al. |
| 6,677,147 | B2 | 1/2004  | Andersen et al. |
| 6,808,915 | B2 | 10/2004 | Glad et al. |
| 7,144,722 | B2 | 12/2006 | Andersen et al. |
| 7,273,745 | B2 | 9/2007  | Andersen et al. |
| 7,601,529 | B2 | 10/2009 | Glad et al. |
| 7,611,882 | B2 | 11/2009 | Bjornvad et al. |
| 2003/0175940 | A1 | 9/2003 | Glad et al. |
| 2005/0244922 | A1 | 11/2005 | Andersen et al. |
| 2005/0250181 | A1 | 11/2005 | Schroder et al. |
| 2006/0165613 | A1 | 7/2006  | Bjoernvad et al. |

FOREIGN PATENT DOCUMENTS

| JP | 11318443 A    | 11/1999 |
| JP | 2000262292 A  | 9/2000  |
| WO | WO 98/06809 A  | 2/1998  |
| WO | WO 98/45393 A2 | 10/1998 |
| WO | WO 99/27083 A1 | 6/1999  |
| WO | WO 99/27084 A1 | 6/1999  |
| WO | WO 00/29560 A1 | 5/2000  |
| WO | WO 00/37627 A1 | 6/2000  |
| WO | WO 00/42145 A1 | 7/2000  |
| WO | WO 00/42155 A1 | 7/2000  |
| WO | WO 00/55309 A1 | 9/2000  |
| WO | WO 00/60063 A1 | 10/2000 |
| WO | WO 02/06442 A1 | 1/2002  |
| WO | WO 02/092741 A2 | 11/2002 |
| WO | WO 03/095638 A1 | 11/2003 |

OTHER PUBLICATIONS

Ito et al., J. Appl. Glycosci., vol. 47, No. 2, pp. 243-251 (2000).
Kao Corp., Database WPI—Accession No. JP11318443 (1999).
Kao Corp., Database WPI—Accession No. AN 2000-642265 or JP 2000253888 (2000).
Kao Corp., Patent Abstracts of Japan, JP 11318443 A (1999).

(Continued)

*Primary Examiner* — Nashaat Nashed
*Assistant Examiner* — William W Moore
(74) *Attorney, Agent, or Firm* — Kristin J. McNamara

(57) ABSTRACT

The present invention relates to pectate lyase variants exhibiting alterations relative to a parent enzyme exhibiting pectate lyase activity as its major enzymatic activity; to a method of producing such enzymes; and to methods for using such enzymes in the textile, detergent and cellulose fiber processing industries. Compared to the parent enzyme, the pectate lyase variants of the present invention exhibit improved stability in detergents.

12 Claims, No Drawings

(56) References Cited

OTHER PUBLICATIONS

Kim et al., Nucleotide Sequence of The Pectate, Database CAPLUS—Accession No. 1994: 550110, document No. 121: 150110 (1994).
Kim et al., Bioscience Biotechnology Biochemistry, vol. 58, No. 5, pp. 947-949 (1994).
Kim et al., Protein Engineering, vol. 14, No. 5, pp. 343-347 (2001).
Nasser et al., Biochimie, vol. 72, No. 9, pp. 689-696 (1990).
Nasser et al., Purification and Characterization, Database Biosis—Accession No. PREV199191043359 (1991).
Nasser et al., FEBS Letters, vol. 335, No. 3, pp. 319-326 (1993).
Nasser et al., Pectate Lyase from *Bacillus subtilis*, Database Biosis—Accession No. PREV199497088806 (1993).
Sakamoto et al., Bioscience Biotechnology Biochemistry, vol. 58, No. 2, pp. 353-358 (1994).
Sakamoto et al., Purification, Characterization, Database Biosis—Accession No. PREV199497268686 (1994).
Sequence alignment of SEQ ID No. 1 in JP 2000-262292 and SEQ ID No. 2 in EP 1 506 292 B1 (document D3), (2011).
Sequence aliignment of SEQ ID No. 2 in EP 1 506 292 B1 and SEQ ID No. 2 in WO 02/06442 (document D5), (2011).
Sequence alignment of SEQ ID No. 2 in EP 1 506 292 B1 and pectate lyase from *Bacillus* sp. YA-14 (document D7), (2011).

PECTATE LYASE VARIANTS

CROSS-REFERENCE TO RELATED APPLICATIONS

This application is a divisional of U.S. application Ser. No. 12/481,922 filed on Jun. 10, 2009 (now U.S. Pat. No. 8,288, 144), which is a divisional of U.S. application Ser. No. 10/513,951 filed on Nov. 9, 2004 (now U.S. Pat. No. 7,601, 529), which is a 35 U.S.C. 371 national application of PCT/DK03/00316 filed May 14, 2003, which claims priority or the benefit under 35 U.S.C. 119 of Danish application no. PA 2002 00746 filed on May 14, 2002 and U.S. provisional application No. 60/381,182 filed on May 18, 2002, the contents of which are fully incorporated herein by reference.

TECHNICAL FIELD

The present invention relates to pectate lyase variants exhibiting alterations relative to a parent enzyme exhibiting pectate lyase activity as its major enzymatic activity; to a method of producing such enzymes; and to methods for using such enzymes in the textile, detergent and cellulose fiber processing industries. Compared to the parent enzyme, the pectate lyase variants of the present invention may exhibit improved stability in detergents.

BACKGROUND OF THE INVENTION

Pectin polymers are important constituents of plant cell walls. Pectin is a hetero-polysaccharide with a backbone composed of alternating homogalacturonan (smooth regions) and rhamnogalacturonan (hairy regions). The smooth regions are linear polymers of 1,4-linked alpha-D-galacturonic acid. The galacturonic acid residues can be methyl-esterified on the carboxyl group to a varying degree, usually in a non-random fashion with blocks of polygalacturonic acid being completely methyl-esterified.

Pectolytic enzymes (pectinases) can be classified according to their preferential substrate, highly methyl-esterified pectin or low methyl-esterified pectin and polygalacturonic acid (pectate), and their reaction mechanism, beta-elimination or hydrolysis. Pectinases can be mainly endo-acting, cutting the polymer at random sites within the chain to give a mixture of oligomers, or they may be exo-acting, attacking from one end of the polymer and producing monomers or dimers. Several pectinase activities acting on the smooth regions of pectin are included in the classification of enzymes provided by the Enzyme Nomenclature (1992) such as pectate lyase (EC 4.2.2.2), pectin lyase (EC 4.2.2.10), polygalacturonase (EC 3.2.1.15), exo-polygalacturonase (EC 3.2.1.67), exo-polygalacturonate lyase (EC 4.2.2.9) and exo-poly-alpha-galacturonosidase (EC 3.2.1.82).

Pectate lyases have been cloned from different bacterial genera such as Erwinia, Pseudomonas, Klebsiella and Xanthomonas. Also from Bacillus subtilis (Nasser et al., 1993, FEBS 335:319-326) and Bacillus sp. YA-14 (Kim et al., 1994, Biosci. Biotech. Biochem. 58:947-949) cloning of a pectate lyase has been described.

The pectate lyases are generally characterized by an alkaline pH optimum and an absolute requirement for divalent cations, $Ca^{2+}$ being the most stimulatory.

It is an object of the present invention to provide a cell-wall degrading enzyme variant, especially a pectate lyase enzyme variant, which exhibits improved performance over the parent pectate lyase when applied, e.g., in detergents or in textile industry processes.

SUMMARY OF THE INVENTION

The inventors have now found that certain amino acid substitutions in cell-wall degrading enzymes especially pectate lyases having a structure including a beta-helix result in enzyme variants having improved performance in the neutral or alkaline pH range compared to the parent enzyme. The pectate lyase variants of the invention, when used in detergent compositions, have improved storage stability, i.e., lower sensitivity to detergents.

Thus, in a first aspect the present invention relates to a pectate lyase variant comprising alterations at one or more positions selected from the group consisting of positions number:

5, 9, 11, 26, 28, 30, 31, 37, 40, 45, 46, 47, 48, 49, 50, 51, 52, 54, 61, 64, 68, 69, 70, 71, 74, 75, 76, 79, 86, 87, 91, 99, 105, 106, 107, 111, 115, 116, 118, 122, 123, 134, 136, 139, 140, 141, 146, 148, 156, 158, 170, 182, 185, 186, 189, 193, 194, 196, 199, 201, 202, 204, 213, 215, 218, 224, 228, 229, 234, 235, 237, 251, 256, 257, 258, 272, 277, 286, 295, 298, 301, 302, 303, 305, 307, 308, 314, 316, 323, 324, 326, 331, 332, 333, 334, 335, 336, 337, 338, 339, 340, 341, 349, 356, 357, 363, 366, 378, 381, 384, 386, 387, 389, 390, 391, 393 and 397, wherein the alteration(s) are independently (i) an insertion of an amino acid downstream of the amino acid which occupies the position, (ii) a deletion of the amino acid which occupies the position, or (iii) a substitution of the amino acid which occupies the position with a different amino acid, and wherein each position corresponds to a position of the amino acid sequence of the pectate lyase having the amino acid sequence of SEQ ID NO: 2, and wherein the parent enzyme is the pectate lyase shown on SEQ ID NO: 2 or a pectate lyase having at least 65% identity to the amino acid sequence of SEQ ID NO: 2.

In a second aspect the present invention relates to a nucleic acid sequence encoding the pectate lyase variant.

In a third aspect of the invention there is provided an expression vector.

In a fourth aspect of the present invention there is provided a microbial host cell transformed with the abovementioned expression vector.

In a fifth aspect of the present invention there is provided a method for improving the detergent stability of a pectate lyase, comprising altering one or more amino acids.

In a sixth aspect of the invention there are provided methods for producing a pectate lyase variant according to the invention comprising culturing a cell into which has been introduced an expression vector as disclosed above, whereby said cell expresses the variant encoded by the nucleic acid sequence and recovering the pectate lyase variant.

The pectate lyase variant of the invention is useful for the treatment of cellulosic material, especially cellulose-containing fiber, yarn, woven or non-woven fabric, treatment of mechanical paper-making pulps or recycled waste paper, and for retting of fibers. The treatment can be carried out during the processing of cellulosic material into a material ready for garment manufacture or fabric manufacture, e.g., in the desizing or scouring step; or during industrial or household laundering of such fabric or garment.

Accordingly, in further aspects the present invention relates to a detergent composition comprising a pectate lyase variant having substantial cell-wall degrading activity; and to use of the pectate lyase variant of the invention for the treatment, e.g., cleaning of cellulose-containing fibers, yarn, woven or non-woven fabric.

Further, additional aspects of the invention relates to an enzyme composition comprising the pectate lyase variant of the invention in combination with other enzymes, and to a cleaning or detergent composition, preferably a laundry or dish wash composition, comprising the pectate lyase variant of the invention.

The pectate lyase variant of the invention, is very effective for use in an enzymatic scouring process in the preparation of cellulosic material, e.g., for proper response in subsequent dyeing operations.

Another aspect of the invention relates to the processing of wine and juice. The enzyme or enzyme preparation may be used in the treatment of mash from fruits and vegetables in order to improve the extractability or degradability of the mash.

Further, an aspect of the invention is the application as an animal feed additive. When added to feed containing plant material from soy bean, rape seed, lupin etc the pectate lyase variant significantly improves the in vivo break-down of plant cell wall material, whereby a better utilization of the plant nutrients by the animal is achieved.

DEFINITIONS

Prior to discussing this invention in further detail, the following terms and conventions will first be defined.

The term "wild-type enzyme" denotes an enzyme, which is endogenous to a naturally occurring microorganism such as a fungus or a bacterium found in Nature.

The term "parent enzyme" as used herein means an enzyme in which modifications are being made to produce the enzyme variants of the invention. A parent enzyme may be an enzyme isolated from a natural source, or an enzyme wherein previous modification(s) have been made while retaining the characteristic activity of the enzyme in question. The parent pectate lyase of the invention may be a wild-type pectate lyase.

The term "enzyme variant" means an enzyme comprising differences in its amino acid sequence from that of the parent enzyme. The differences comprise substitutions, deletions and/or insertions as compared to the parent enzyme.

The term "ortholog" (or "species homolog") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector it is to be introduced. Thus, the vector may be an autonomously replicating vector, i.e., a vector existing as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinant expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, 1985, Nature 316:774-78). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e., "homologous impurities" (see below)). It is preferred to provide the protein in a greater than 40% pure form, more preferably greater than 60% pure form. Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity, e.g., another polypeptide than the polypeptide of the invention, which originate from the homologous cell where the polypeptide of the invention is originally obtained from.

The term "obtained from" as used herein in connection with a specific microbial source, means that the polynucleotide and/or polypeptide is produced by the specific source, or by a cell in which a gene from the source have been inserted.

The term "operably linked", when referring to DNA segments, denotes that the segments are arranged so that they function in concert for their intended purposes, e.g., transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "pectin" denotes pectate, polygalacturonic acid, and pectin which may be esterified to a higher or lower degree.

The term "pectinase" denotes a pectinase enzyme defined according to the art where pectinases are a group of enzymes that cleave glycosidic linkages of pectic substances mainly poly(1,4-alpha-D-galacturonide and its derivatives (see reference Sakai et al., Pectin, pectinase and protopectinase: production, properties and applications, *Advances in Applied Microbiology* 39:213-294 (1993)).

Preferably a pectinase of the invention is a pectinase enzyme which catalyzes the random cleavage of alpha-1,4-glycosidic linkages in pectic acid also called polygalacturonic acid by transelimination such as the enzyme class polygalacturonate lyase (EC 4.2.2.2) (PGL) also known as poly(1,4-alpha-D-galacturonide) lyase also known as pectate lyase.

The term "thermostability" or "thermal stability" is intended to mean the stability of the protein to thermal influence. All enzyme proteins destabilizes and eventually degrades with increasing temperature, each enzyme protein having a certain temperature range wherein the protein is stable and retains its enzymatic activity. Increased thermostability means that the enzyme protein may retain its enzymatic activity and/or exhibit a higher relative activity at increased temperatures.

The term "detergent stability" or "storage stability" is intended to mean the stability of the protein in a formulation containing detergents, e.g., anionic surfactants. Anionic surfactants are characterized by the combination of an anionic group and a hydrophobic tail. When binding to the protein, a positively charged residue like Lysine or Arginine, and a hydrophobic area are thus likely interaction points. Similarly the dynamic of particularly flexible regions is opening up for the accessibility to amino acids normally buried in the internal of the protein. These residues are typically hydrophobic and are thus attractive for the tail of the surfactant. A chemical interaction between enzyme and surfactant will with high certainty leave the enzyme inactive. Thus improved detergent- or storage stability means that at a certain detergent concentration and temperature, a greater enzymatic activity will be retained after a certain period of time (greater residual activity).

Accordingly, thermostability and detergent stability are two independent characteristics of a protein or an enzyme.

The pectate lyase variants of the invention having improved detergent stability may exhibit at least 120% (preferably at least 140%, more preferably at least 160%, even more preferably at least 180%, even more preferably at least 200%, most preferably at least 250% and in particular at least 300%) residual activity compared to the parent pectate lyase, when subjected to the analysis method described in Example 1.

Protein Numbering

In the context of this invention, a specific numbering of amino acid residue positions in cell-wall degrading enzymes, especially pectate lyase enzymes, are employed. For example, by aligning the amino acid sequences of known pectate lyases it is possible to unambiguously allot an amino acid position number to any amino acid residue in any pectate lyase enzyme, if its amino acid sequence is known.

Using the numbering system originating from the amino acid sequence of the pectate lyase encoded by the polynucleotide present in the plasmid of the strain *Bacillus subtilis* DSM 14218, disclosed in SEQ ID NO: 2, aligned with the amino acid sequence of a number of other pectate lyases, it is possible to indicate the position of an amino acid residue in a pectate lyase enzyme unambiguously.

In describing the various cell-wall degrading enzyme variants produced or contemplated according to this invention, the following nomenclatures are adapted for ease of reference:

Substitutions:

[Original amino acid; Position; Substituted amino acid]

Accordingly, the substitution of serine with isoleucine in position 72 is designated as S72I.

Multiple mutations are separation by addition marks ("+"), e.g., M169I+F198V, representing mutations in positions 169 and 198 substituting methionine (M) with isoleucine (I), and phenylalanine (F) with valine (V), respectively.

Deletions:

A deletion of glycine in position 195 will be indicated by:
Gly195* or G195*

Correspondingly the deletion of more than one amino acid residue, such as the deletion of glycine and leucine in positions 195 and 196 will be designated
Gly195*+Leu196* or G195*+L196*

Insertions:

The insertion of an additional amino acid residue such as, e.g., a lysine after G195 is indicated by:
Gly195GlyLys or G195GK;

or, when more than one amino acid residue is inserted, such as, e.g., a Lys and Ala after G195 this will be indicated as:
Gly195GlyLysAla or G195GKA In such cases the inserted amino acid residue(s) are numbered by the addition of lower case letters to the position number of the amino acid residue preceding the inserted amino acid residue(s). In the above example the sequences 194 to 196 would thus be changed from:

```
194 195 196
 A - G - L
to 194 195 195a 195b 196
 A - G - K - A - L
```

In cases where an amino acid residue identical to the existing amino acid residue is inserted it is clear that degeneracy in the nomenclature arises. If for example a glycine is inserted after the glycine in the above example this would be indicated by G195GG. The same actual change could just as well be indicated as A194AG for the change from:

```
194 195 196
 A - G - L
to 194 195 195a 196
```

```
                    -continued
                  A - G - G - L
                  or 194 194a 195 196
```

Such instances will be apparent to the skilled person and the indication G195GG and corresponding indications for this type of insertions are thus meant to comprise such equivalent degenerate indications.

All positions referred to herein by pectate lyase numbering refer, unless otherwise stated, to the numbering described above, and are determined relative to the amino acid sequence of the pectate lyase encoded by the polynucleotide present in the plasmid of the strain *Bacillus subtilis* DSM 14218, disclosed in SEQ ID NO: 2.

DETAILED DESCRIPTION OF THE INVENTION

The present invention is pertaining to variants of a parent pectate lyase (EC 4.2.2.2). The variants have improved properties compared to the parent enzyme, especially the detergent stability or storage stability in detergent compositions is improved.

In the process of improving the properties of the parent pectate lyase, the inventors found that alterations of specific amino acids in the parent polypeptide backbone would significantly alter the detergent stability of the enzyme.

Polynucleotides

Within preferred embodiments of the invention it is contemplated that a polynucleotide encoding the parent enzyme of the pectate lyase variant of the invention will hybridize to similar sized regions of the corresponding polynucleotide of SEQ ID NO: 1, or a sequence complementary thereto, under at least medium stringency conditions, preferably high stringency conditions.

In particular polynucleotides of the invention will hybridize to a denatured double-stranded DNA probe comprising either the full variant sequence corresponding to positions 1-1200 of SEQ ID NO: 1 with proper sequence alterations corresponding to actual amino acid substitutions made or any probe comprising a variant subsequence thereof having a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al., 1989) for 10 min, and prehybridization of the filter in a solution of 5×SSC, 5×Denhardt's solution (Sambrook et al., 1989), 0.5% SDS and 100 microgram/ml of denatured sonicated salmon sperm DNA (Sambrook et al., 1989), followed by hybridization in the same solution containing a concentration of 10 ng/ml of a random-primed (Feinberg and Vogelstein, 1983, *Anal. Biochem.* 132:6-13), 32P-dCTP-labeled (specific activity higher than 1×109 cpm/microgram) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using an X-ray film.

As previously noted, the polynucleotides encoding the pectate lyase variants of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having pectate lyase activity of the invention are then identified and isolated by, for example, hybridization or PCR.

Species homologues of the parent pectate lyase used in preparation of the pectate lyase variants of the invention can be cloned using information and compositions provided by the present invention in combination with conventional cloning techniques. For example, DNA can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA encoding a polypeptide having pectate lyase activity of the invention can then be isolated by a variety of methods, such as by probing with a complete or partial DNA or with one or more sets of degenerate probes based on the disclosed sequences. A DNA can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the pectate lyase cloned from *B. subtilis* strain deposited as IFO 3134, or by an activity test relating to a polypeptide having pectate lyase activity. Similar techniques can also be applied to the isolation of genomic clones.

The polypeptide encoding part of the DNA sequence cloned a plasmid present in *Bacillus subtilis* DSM 14218 and/or an analogue DNA sequence of the invention may be cloned from a strain of the bacterial species *Bacillus subtilis*, preferably the strain deposited as IFO 3134, producing the enzyme with pectin degrading activity, or another or related organism as described herein.

Alternatively, the analogous sequence may be constructed on the basis of the DNA sequence obtainable from a plasmid present in *Bacillus subtilis* DSM 14218 e.g., be a sub-sequence thereof, and/or by introduction of nucleotide substitutions which do not give rise to another amino acid sequence of the pectate lyase encoded by the DNA sequence, but which corresponds to the codon usage of the host organism intended for production of the enzyme, or by introduction of nucleotide substitutions which may give rise to a different amino acid sequence (i.e., a variant of the pectin degrading enzyme of the invention).

Polypeptides

The sequence of amino acids no. 1-399 of SEQ ID NO: 2 is a mature pectate lyase sequence corresponding to a wild-type pectate lyase from the species *Bacillus subtilis* deposited as IFO 3134 (Institute for Fermentation, Osaka, 17-85, Jusohonmachi 2-chome, Yodagawa-ku, Osaka 532-8686, Japan).

The present invention also provides pectate lyase variants of polypeptides that are substantially homologous to the polypeptides of SEQ ID NO: 2 and its species homologs (paralogs or orthologs). The term "substantially homologous" is used herein to denote polypeptides having 70%, more preferably at least 85%, and even more preferably at least 90%, sequence identity to the sequence shown in SEQ ID NO: 2 or its orthologs or paralogs. Such polypeptides will more preferably be at least 95% identical, and most preferably 98% or more identical to the sequence shown in SEQ ID NO: 2 or its orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman and Wunsch, 1970, *Journal of Molecular Biology* 48: 443-453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

The parent pectate lyase is preferably derived from a microorganism, preferably from a bacterium, an archea or a fungus, especially from a bacterium such as a bacterium belonging to *Bacillus*, preferably to an alkalophilic *Bacillus* strain which may be selected from the group consisting of the species *Bacillus subtilis* and highly related *Bacillus* species in which all species preferably are at least 95%, even more preferably at least 98%, homologous to *Bacillus subtilis* based on aligned 16S rDNA sequences. The parent pectate lyases of the invention are substantially homologous to the polypeptides of SEQ ID NO: 2 and its species homologs (paralogs or orthologs). The term "substantially homologous" is used herein to denote polypeptides having 70%, more preferably at least 85%, and even more preferably at least 90%, sequence identity to the sequence shown in SEQ ID NO: 2 or its orthologs or paralogs. Such polypeptides will more preferably be at least 95% identical, and most preferably 98% or more identical to the sequence shown in SEQ ID NO: 2 or its orthologs or paralogs.

Substantially homologous parent proteins and polypeptides are characterized as having one or more amino acid substitutions, deletions or additions. These changes are preferably of a minor nature, that is conservative amino acid substitutions (see Table 1) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, protein A (Nilsson et al., 1985, *EMBO J.* 4:1075; Nilsson et al., 1991, *Methods Enzymol.* 198:3. See, in general Ford et al., 1991, *Protein Expression and Purification* 2: 95-107, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions.

TABLE 1

Conservative amino acid substitutions

| | |
|---|---|
| Basic: | arginine |
| | lysine |
| Acidic: | glutamic acid |
| | aspartic acid |
| Polar: | glutamine |
| | asparagines |
| | serine |
| | threonine |
| | cysteine |

TABLE 1-continued

Conservative amino acid substitutions

| | |
|---|---|
| Hydrophobic: | leucine |
| | isoleucine |
| | valine |
| | proline |
| | methionine |
| Aromatic/ | phenylalanine |
| Heteroaromatic: | tryptophan |
| | tyrosine |
| | histidine |
| Small: | glycine |
| | alanine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the pectate lyase polypeptides of the present invention can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., pectate lyase activity) to identify amino acid residues that are critical to the activity of the molecule. See also, Hilton et al., 1996, *J. Biol. Chem.* 271:4699-4708. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., 1992, *Science* 255:306-312; Smith et al., 1992, *J. Mol. Biol.* 224:899-904; Wlodaver et al., 1992, *FEBS Lett.* 309:59-64. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (1988, *Science* 241:53-57), Bowie and Sauer (1989, *Proc. Natl. Acad. Sci. USA* 86:2152-2156), WO 95/17413, or WO 95/22625. Briefly, these authors disclose methods for simultaneously randomizing two or more positions in a polypeptide, or recombination/shuffling of different mutations (WO 95/17413, WO 95/22625), followed by selecting for functional a polypeptide, and then sequencing the mutagenized polypeptides to determine the spectrum of allowable substitutions at each position. Other methods that can be used include phage display (e.g., Lowman et al., 1991, *Biochem.* 30:10832-10837; Ladner et al., U.S. Pat. No. 5,223,409; Huse, WO 92/06204) and region-directed mutagenesis (Derbyshire et al., 1986, *Gene* 46:1456; Ner et al., 1988, *DNA* 7:127).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 1 to 399 of SEQ ID NO: 2 and retain the pectate lyase activity of the parent enzyme.

However, the very same methods are also useful for providing the pectate lyase variants of the invention having more advantageous properties than the wild-type protein. Using these methods, the present inventors have identified a number of positions in which the wild-type pectate lyase of SEQ ID NO: 2 may advantageously by substituted in order to prepare variants with improved properties.

Preferred pectate lyase variants of the inventions are substituted in one or more of the following positions (numbering relative to SEQ ID NO: 2): 5, 9, 11, 26, 28, 30, 31, 37, 40, 45, 46, 47, 48, 49, 50, 51, 52, 54, 61, 64, 68, 69, 70, 71, 74, 75, 76, 79, 86, 87, 91, 99, 105, 106, 107, 111, 115, 116, 118, 122, 123, 134, 136, 139, 140, 141, 146, 148, 156, 158, 170, 182, 185, 186, 189, 193, 194, 196, 199, 201, 202, 204, 213, 215, 218, 224, 228, 229, 234, 235, 237, 251, 256, 257, 258, 272, 277, 286, 295, 298, 301, 302, 303, 305, 307, 308, 314, 316, 323, 324, 326, 331, 332, 333, 334, 335, 336, 337, 338, 339, 340, 341, 349, 356, 357, 363, 366, 378, 381, 384, 386, 387, 389, 390, 391, 393 and 397.

Preferred variants of the present invention further comprise variants in which the overall charge of the enzyme has been made more negative. In such variants positively charged amino acids may have been replaced and/or amino acids, which are negatively charged under the application conditions, have been introduced.

Thus, in accordance herewith, preferred variants may have had replaced an amino acid residue being partly or fully positively charged under application conditions, i.e., a His, Lys or an Arg. Further, preferred variants may have had replaced any residue by an amino acid residue with a negative charge under application conditions, i.e., Asp, Glu, and Tyr.

Especially preferred variants are those in which a lysine residue in one or more of the following positions (numbering relative to SEQ ID NO: 2): 26, 47, 54, 59, 71, 79, 87, 90, 99, 100, 115, 118, 139, 148, 213, 218, 247, 257, 263, 265, 274, 314, 317, 334, 386 and 397, has been replaced.

Likewise, especially preferred variants are those in which an arginine residue in one or more of the following positions (numbering relative to SEQ ID NO: 2): 38, 110, 112, 120, 155, 206, 217, 272, 279, 282 and 284, has been replaced.

Further, preferred variants are also those in which a histidine residue in one or more of the following positions (numbering relative to SEQ ID NO: 2): 5, 31, 193, 198, 221, 222, 243, 245, 269, 270, 289, 376 and 384, has been replaced.

Preferred variant pectate lyase enzymes have been modified in order to change the binding constant for $Ca^{2+}$, and thereby improving the calcium-depletion stability. In a pectate lyase of the present invention, the three amino acid residues D184, D223 and D227 are coordinating the binding of $Ca^{2+}$ at the primary calcium binding site. By recruiting a fourth amino acid residue in this coordination it is possible to change the binding constant for $Ca^{2+}$. The presence of $Ca^{2+}$ at the primary calcium binding site may influence either the catalytic event (by reducing the pKa of the catalytic residue), the alignment of the substrate or determine whether the enzyme functions as a hydrolase or a lyase (the presence of $Ca^{2+}$ being a prerequisite for lyase activity). Such variants with improved calcium-depletion stability may comprise one of the substitutions Q182D and Q182E.

Further examples of preferred variants are those with improved oxidation stability in which an oxidation labile amino acid residue has been replaced. By "oxidation labile" are meant amino acids holding a sulphur- or a hydroxyl-group, e.g., methionine, cysteine, threonine, serine and tyrosine. Preferred variants are those in which an oxidation labile amino acid residue in one or more of the following positions (numbering relative to SEQ ID NO: 2): 64, 122, 199 and 237 have been replaced.

Further examples of preferred variants are those holding an amino acid substitution in a flexible residue, wherein a less flexible amino acid residue has been introduced. In the present context the term "flexible" refers to the number of possible phi and psi angles of the C-alpha atom in the amino acid. The flexibility of the peptide backbone is limited by steric hindrance of the atoms bound to the C-alpha atom. In general only the amino acid side chain differs from one residue to the other, thus the size of the side chain (the Van der Waals radius) determines the flexibility. A glycine has the smallest side chain, a hydrogen atom; therefore a glycine residue introduces more flexibility. The opposite situation applies for proline, where the possible conformations are limited not only by a large side chain but also due to the ring structure. Thus a proline residue is less flexible than average, and gives stiffness and stability to the peptide.

Such less flexible variants include in particular, but are not limited to, variants in which a glycine residue have been substituted with any of the other 19 naturally occurring amino acids or variants in which any amino acid have been substituted with a proline residue. In especially preferred variants a less flexible amino acid residue has been introduced in one or more of the following regions (numbering of positions relative to SEQ ID NO: 2): 26-31, 45-50, 66-72, 81-89, 90-106, 134-137, 169-178, 210-217, 253-262, 275-286, 297-308, 328-343, 354-356, 361-365, 368-372 and 376-379.

In a preferred embodiment of the present invention, the *Bacillus subtilis* pectate lyase variant comprises at least one substituted amino acid residue selected from the group consisting of: H5R, E9G, N11Y, K26Q, S28T, S30F, S30P, S30T, H31N, N37D, Q40E, L45V, G46D, K47N, K47R, D48E, D48P, T49P, N50D, N50L, N50Y, T51Y, T52M, K54V, T61A, M64F, D68*, N69*, L70*, K71*, K71E, G74D, L75A, L75P, N76D, K79A, D86N, K87A, K87E, A91E, K99I, K99N, K99R, T105A, T105P, L106Q, E107K, A111E, K115A, K115I, K115N, K115Q, N116D, K118A, K118E, M122E, M122K, M122N, M122Q, V123I, S134L, T136S, K139E, K139F, K139I, K139M, K139N, K139S, I140V, V141G, V141E, V141L, V141N, Q146F, Q146H, Q146I, Q146V, K148E, K148Q, N156S, E158N, D170N, Q182D, Q182E, N185H, I186H, N189D, H193Y, I194V, I196V, C199N, C199S, F201L, N202K, G204R, K213E, K213N, K213T, F215Y, K218E, K218L, K218P, G224S, A228I, S229T, Y234H, I235V, M237I, F251I, S256C, K257E, K257N, T258I, L286Y, R272C, R272H, R272Y, V277D, G286A, Y295H, S298N, S301Y, S302A, D303S, A305P, S307R, Y308S, K314N, S316F, N323M, V324A, D326N, S331P, S331T, A332P, A333E, K334E, T335S, T335P, I336S, S337C, S337K, S337L, S337R, V338E, V338Y, F339I, S340A, S340K, S340N, S340P, S340Q, G341S, G349R, Q356H, I357V, N363S, S366N, T378G, T378S, A381D, H384N, K386P, K386R, S387A, V389I, I390N, I390T, S391N, A393V and K397D.

It is at present contemplated that one or more of these substitutions either alone or in combination increase the detergent stability of the pectate lyase variant when compared to the parent enzyme.

Preferred multiple substitutions which increase the detergent stability include:

A228I+F251I,
S134L+K257E,
K115I+K213E,
K139I+K213N,
H5R+K257N+S302A,
K99I+I196V,
K115A+K118A,
K115A+K118A+M122N,
V141E+C199S+K213E,
K115I+Q146H,
K71E+K118E,
T49P+N156S,
K314N+S340P,
V141E+I235V,
G46D+K257N,
S28T+S30F+K334E+N363S,
D48E+L106Q+I140V+F215Y+K218E,
H193Y+S256C+V389I+A393V,
E9G+H31N+N50D+L106Q+A111E+T136S+V141L+ F201L+N202K+F215Y+G286A+A381D+H384N, K213N+ T258I,
E9G+H31N+L106Q+D303S+A305P+T335S+H384N+ S391N,
E9G+H31N+D48E+L106Q+A111E+S301Y+D303S+ A305P+T378S+H384N+S391N,
L45V+N50Y+N185H,
N11Y+K87E+K99N,
E9G+D48E+L106Q+S316F+A381D,
S30P+K115I+K139I+Q146H+S337C,
E9G+H31N+D48E+L106Q+I114V+F215Y+D303S+ A305P+T378S+H384N+S391N,
H31N+T105A+L106Q+A111E+V141L+K218E+ D303S+A305P+D326N+T335S+H384N+S391N,
K26Q+K47N+L106Q+I140V+F215Y+D303S+A305P+ T378S+H384N+S391N,
D48E+L106Q+I140V+F215Y+D303S+A305P+T378S+ H384N+S391N,
K213T+K218L+A305P,
M64F+K213T+K218L+A305P,
M64F+M122K+K118E+K213T+K218L+A305P,
K139I+Q146H+K257N+S337C,
M64F+K139I+Q146H+S337C, K139I+Q146H+S337C and
D48P+M64F+T105P+K139I+Q146H+K213T+K218P+ T258I+A305P+S331P+S337K.

Protein Production

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Bacterial cells, particularly cultured cells of gram-positive organisms, are preferred. Gram-positive cells from the genus of *Bacillus* are especially preferred, such as *B. licheniformis, B. lentus, B. brevis, B. stearothermophilus, B. alkalophilus, B. amyloliquefaciens, B. coagulans, B. circulans, B. lautus, B. thuringiensis, B. agaradherens*, or in particular *B. subtilis*.

Techniques for manipulating cloned DNA molecules and introducing exogenous DNA into a variety of host cells are disclosed by Sambrook et al., Molecular Cloning: A Laboratory Manual, 2nd ed., Cold Spring Harbor Laboratory Press, Cold Spring Harbor, N.Y., 1989; Ausubel et al. (eds.), Current Protocols in Molecular Biology, John Wiley and Sons, Inc., NY, 1987; and (*Bacillus subtilis* and Other Gram-Positive Bacteria, Sonensheim et al., 1993, American Society for Microbiology, Washington D.C.), which are incorporated herein by reference.

In general, a DNA sequence encoding a pectate lyase of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the polypeptide, or may be derived from another secreted protein or synthesized de novo. Numerous suitable secretory signal sequences are known in the art and reference is made to *Bacillus subtilis* and Other Gram-Positive Bacteria, Sonenshein et al., 1993 (American Society for Microbiology, Washington D.C.); and Cutting, S. M. (eds.) "Molecular Biological Methods for *Bacillus*", (John Wiley and Sons, 1990) for further description of suitable secretory signal sequences especially for secretion in a *Bacillus* host cell. The secretory signal sequence is joined to the DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The fermentation may be carried out by cultivation of the host cell under aerobic conditions in a nutrient medium containing carbon and nitrogen sources together with other essential nutrients, the medium being composed in accordance with the principles of the known art. The medium may be a complex rich medium or a minimal medium. The nitrogen source may be of inorganic and/or organic nature. Suitable inorganic nitrogen sources are nitrates and ammonium salts. Among the organic nitrogen sources quite a number are used regularly in fermentations. Examples are soybean meal, casein, corn, corn steep liquor, yeast extract, urea and albumin. Suitable carbon sources are carbohydrates or carbohydrate containing materials. Preferably the nutrient medium contains pectate, polygalacturonic acid and/or pectin esterified to a higher or lower degree as carbon source and/or inducer of pectinase production. Alternatively, the medium contains a pectin rich material such as soybean meal, apple pulp or citrus peel.

The cultivation may preferably be conducted at alkaline pH values such as at least pH 8 or at least pH 9, which can be obtained by addition of suitable buffers such as sodium carbonate or mixtures of sodium carbonate and sodium bicarbonate after sterilisation of the growth medium.

Protein Isolation

When the expressed recombinant polypeptide is secreted the polypeptide may be purified from the growth media. Preferably the expression host cells are removed from the media before purification of the polypeptide (e.g., by centrifugation).

When the expressed recombinant polypeptide is not secreted from the host cell, the host cell are preferably disrupted and the polypeptide released into an aqueous "extract" which is the first stage of such purification techniques. Preferably the expression host cells are removed from the media before the cell disruption (e.g., by centrifugation).

The cell disruption may be performed by conventional techniques such as by lysozyme digestion or by forcing the cells through high pressure. See (Robert K. Scobes, Protein Purification, Second edition, Springer-Verlag) for further description of such cell disruption techniques.

Whether or not the expressed recombinant polypeptides (or chimeric polypeptides) are secreted or not it can be purified using fractionation and/or conventional purification methods and media.

Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with Fast-Flow Sepharose (Pharmacia Biotech, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers.

Selection of a particular method is a matter of routine design and is determined in part by the properties of the chosen support. See, for example, Affinity Chromatography: Principles & Methods, Pharmacia LKB Biotechnology, Uppsala, Sweden, 1988.

Polypeptides of the invention or fragments thereof may also be prepared through chemical synthesis. Polypeptides of the invention may be monomers or multimers; glycosylated or non-glycosylated; pegylated or non-pegylated; and may or may not include an initial methionine amino acid residue.

Accordingly, in a further aspect, the present invention also relates to a method of producing the enzyme preparation of the invention, the method comprising culturing a microorganism capable of producing the pectate lyase variant under conditions permitting the production of the enzyme, and recovering the enzyme from the culture. Culturing may be carried out using conventional fermentation techniques, e.g., culturing in shake flasks or fermentors with agitation to ensure sufficient aeration on a growth medium inducing production of the pectate lyase variant. The growth medium may contain a conventional N-source such as peptone, yeast extract or casamino acids, a reduced amount of a conventional C-source such as dextrose or sucrose, and an inducer such as pectate or pectin or composit plant substrates such as cereal brans (e.g., wheat bran or rice husk). The recovery may be carried out using conventional techniques, e.g., separation of bio-mass and supernatant by centrifugation or filtration, recovery of the supernatant or disruption of cells if the enzyme of interest is intracellular, perhaps followed by further purification as described in EP 406314 or by crystallization as described in WO 97/15660.

In yet another aspect, the present invention relates to an isolated pectate lyase variant having the properties described above and which is free from homologous impurities, and is produced using conventional recombinant techniques.

Methods and Uses

Microtiter Assay for Quantification of Pectate Lyase Activity

Pectate lyase cleaves polygalacturonic acid through a trans elimination mechanism. This means that it leaves a double C—C bond for each substrate split. This bond absorbs at 235 nm allowing direct detection of pectate lyase action on soluble polygalacturonic acid by measuring absorbance at that wavelength.

An enzyme sample is diluted in assay buffer (100 mM Tris-HCl, 0.68 mM $CaCl_2$, pH 8.0) to a concentration between 5 and 100 ng/ml. If the enzyme sample contains detergent it should be diluted at least a 1000-fold with respect to detergent.

100 microliters of the enzyme buffer dilution is mixed with 100 microliters substrate (1% (w/v) polygalacturonic acid from Sigma, P-3850, stirred in assay buffer for at least 15 min and centrifuged for 5 min at 2300 g, supernatant is used.) in a heating plate and heated to 40° C. for 10 min. in a heating block, preferably a PCR machine or equipment of equivalent accuracy and heating speeds.

100 microliters enzyme/substrate solution is mixed with 100 microliters stop reagent (50 mM $H_3PO_4$) in a UV-transparent microtiter plate. The UV plate is shaken briefly and gently, and the absorbance at 235 nm is measured in a microtiter spectrometer (Molecular Devices, SpectraMAX 190). The absorbance readings are corrected for background absorbance by subtracting the absorbance of a control sample, run without enzyme added, to all measured values.

A standard curve based on the activity of the pectate lyase of SEQ ID NO: 2 (from *Bacillus subtilis* deposited as IFO 3134) was linear between 2.5 and 100 ng/ml enzyme in the reaction mixture:

| Enzyme dose (ng/ml) | Absorbance at 235 nm (AU), background subtracted |
|---|---|
| 0 | 0.00 |
| 2.5 | 0.03 |
| 5 | 0.07 |
| 10 | 0.16 |
| 15 | 0.26 |
| 25 | 0.42 |
| 50 | 0.85 |
| 100 | 1.83 |

Alternatively, catalytic activity of pectate lyase can be determined by the viscosity assay, APSU.

Viscosity Assay, APSU

APSU units: The APSU assay measures the change in viscosity of a solution of polygalacturonic acid in the absence of added calcium ions.

A 5% w/v solution of sodium polygalacturonate (Sigma P-1879) is solubilised in 0.1 M glycine buffer, pH 10. 4 ml of this solution are preincubated for 5 min at 40° C. Then, 250 microliters of the enzyme (or enzyme dilution) are added, after which the reaction is mixed for 10 sec on a mixer at the highest speed and incubated for 20 min at 40° C. or at another temperature.

Viscosity is measured using a MIVI 600 viscometer (Sofraser, 45700 Villemandeur, France). Viscosity is measured as mV after 10 sec. For calculation of APSU units the following standard curve is used:

| APSU/ml | | | | | | | | | |
|---|---|---|---|---|---|---|---|---|---|
| | 0.00 | 4.00 | 9.00 | 14.00 | 19.00 | 24.00 | 34.00 | 49.00 | 99.00 |
| mV | 300 | 276 | 249 | 227 | 206 | 188 | 177 | 163 | 168 |

Use in the Detergent Industry

In further aspects, the present invention relates to a detergent composition comprising the pectate lyase variant or pectate lyase variant preparation of the invention, and to a process for machine treatment of fabrics comprising treating fabric during a washing cycle of a machine washing process with a washing solution containing the pectate lyase variant or pectate lyase variant preparation of the invention.

Typically, the detergent composition of the invention comprises conventional ingredients such as surfactants (anionic, nonionic, zwitterionic, amphoteric), builders, and other ingredients, e.g., as described in WO 97/01629 which is hereby incorporated by reference in its entirety.

Use in the Textile and Cellulosic Fiber Processing Industries

The pectate lyase variant of the present invention can be used in combination with other carbohydrate-degrading enzymes (for instance hemicellulases, such as arabinanase, xyloglucanase, mannanase and pectinase) for biopreparation of fibers or for cleaning of fibers in combination with detergents. Cotton fibers consist of a primary cell wall layer containing pectin and a secondary layer containing mainly cellulose. Under cotton preparation or cotton refining part of the primary cell wall will be removed. The present invention relates to either help during cotton refining by removal of the primary cell wall, or during cleaning of the cotton to remove residual pectic substances and prevent graying of the textile.

In the present context, the term "cellulosic material" is intended to mean fibers, sewn and unsewn fabrics, including knits, wovens, denims, yarns, and toweling, made from cotton, cotton blends or natural or manmade cellulosics (e.g., originating from xylan-containing cellulose fibers such as from wood pulp) or blends thereof. Examples of blends are blends of cotton or rayon/viscose with one or more companion material such as wool, synthetic fibers (e.g., polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g., rayon/viscose, ramie, hemp, flax/linen, jute, cellulose acetate fibers, lyocell).

The preparation of the present invention is useful in the cellulosic fiber processing industry for the pre-treatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in preparation are a. Desizing (for woven goods) using polymeric size like, e.g., starch, CMC or PVA is added before weaving in order to increase the warp speed. This material must be removed before further processing.

b. Scouring, the aim of which is to remove non-cellulosic material from the cotton fiber, especially the cuticle (mainly consisting of waxes) and primary cell wall (mainly consisting of pectin, protein and xyloglucan). A proper wax removal is necessary for obtaining a high wettability, being a measure for obtaining a good dyeing. Removal of the primary cell wall—especially the pectins—improves wax removal and ensures a more even dyeing. Further this improves the whiteness in the bleaching process. The main chemical used in scouring is sodium hydroxide in high concentrations, up to 70 g/kg cotton and at high temperatures, 80-95° C.; and c. Bleaching; normally the scouring is followed by a bleach using hydrogen peroxide as the oxidizing agent in order to obtain either a fully bleached (white) fabric or to ensure a clean shade of the dye.

A one step combined scour/bleach process is also used by the industry. Although preparation processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8-15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period, which, in the case of cold pad-batch, might be one or more days.

Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative processes are often used. The most common sizing agent for cotton fabric is based upon starch. Therefore most often, woven cotton fabrics are desized by a combination of hot water, the enzyme alpha-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath which generally ranges from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following preparation processes: scouring and bleaching.

The scouring process removes much of the non-cellulosic compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80-100° C., employing strongly alkaline solutions, pH 13-14, of the scouring agent. Due to the non-specific nature of chemical processes not only are the impurities but the cellulose itself is attacked, leading to damages in strength or other desirable fabric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

In the examples below it is shown that the scouring step can be carried out using the pectate lyase or pectate lyase preparation of the present invention a temperature of about 50-80° C. and a pH of about 7-11, thus substituting or supplementing the highly causticizing agents. An optimized enzymatic process ensures a high pectin removal and full wettability.

Degradation or Modification of Plant Material

The enzyme or enzyme preparation according to the invention is preferably used as an agent for degradation or modification of plant cell walls or any pectin-containing material originating from plant cells walls due to the high plant cell wall degrading activity of the pectate lyase variant of the invention.

The pectate lyase variant of the present invention may be used alone or together with other enzymes like glucanases, pectinases and/or hemicellulases to improve the extraction of oil from oil-rich plant material, like soy-bean oil from soybeans, olive-oil from olives or rapeseed-oil from rape-seed or sunflower oil from sunflower.

The pectate lyase variant of the present invention may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions. The separation process may be performed by use of methods known in the art.

The pectate lyase variant of the invention may also be used in the preparation of fruit or vegetable juice in order to increase yield, and in the enzymatic hydrolysis of various plant cell wall-derived materials or waste materials, e.g., from wine or juice production, or agricultural residues such as vegetable hulls, bean hulls, sugar beet pulp, olive pulp, potato pulp, and the like.

The plant material may be degraded in order to improve different kinds of processing, facilitate purification or extraction of other component than the galactans like purification of pectins from citrus, improve the feed value, decrease the water binding capacity, improve the degradability in waste water plants, improve the conversion of plant material to ensilage, etc.

By means of an enzyme preparation of the invention it is possible to regulate the consistency and appearance of processed fruit or vegetables. The consistency and appearance has been shown to be a product of the actual combination of enzymes used for processing, i.e., the specificity of the enzymes with which the pectate lyase variant of the invention is combined. Examples include the production of clear juice, e.g., from apples, pears or berries; cloud stable juice, e.g., from apples, pears, berries, citrus or tomatoes; and purees, e.g., from carrots and tomatoes.

The pectate lyase variant of the invention may be used in modifying the viscosity of plant cell wall derived material. For instance, the pectate lyase variant may be used to reduce the viscosity of feed containing galactan and to promote processing of viscous galactan containing material. The viscosity reduction may be obtained by treating the galactan containing plant material with an enzyme preparation of the invention under suitable conditions for full or partial degradation of the galactan containing material The pectate lyase variant can be used, e.g., in combination with other enzymes for the removal of pectic substances from plant fibers. This removal is essential, e.g., in the production of textile fibers or other cellulosic materials. For this purpose plant fiber material is treated with a suitable amount of the pectate lyase of the invention under suitable conditions for obtaining full or partial degradation of pectic substances associated with the plant fiber material.

Animal Feed Additive

Pectate lyase variants of the present invention may be used for modification of animal feed and may exert their effect either in vitro (by modifying components of the feed) or in vivo. The pectate lyase variant is particularly suited for addition to animal feed compositions containing high amounts of arabinogalactans or galactans, e.g., feed containing plant material from soy bean, rape seed, lupin etc. When added to the feed the pectate lyase variant significantly improves the in vivo break-down of plant cell wall material, whereby a better utilization of the plant nutrients by the animal is achieved. Thereby, the growth rate and/or feed conversion ratio (i.e., the weight of ingested feed relative to weight gain) of the animal is improved. For example the indigestible galactan is degraded by pectate lyase, e.g., in combination with beta-galactosidase, to galactose or galactooligomers which are digestible by the animal and thus contribute to the available energy of the feed. Also, by the degradation of galactan the pectate lyase may improve the digestibility and uptake of non-carbohydrate feed constituents such as protein, fat and minerals.

For further description reference is made to PCT/DK96/00443 and a working example herein.

Wine and Juice Processing

The enzyme or enzyme preparation of the invention may be used for de-pectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme or enzyme preparation may be used in the treatment of mash from fruits and vegetables in order to improve the extractability or degradability of the mash. For instance, the enzyme preparation may be used in the treatment of mash from apples and pears for juice production, and in the mash treatment of grapes for wine production.

The applicability of pectate lyase variants with improved detergent stability is appreciated whenever the variants are used in an environment comprising surfactants.

DETERGENT DISCLOSURE AND EXAMPLES

Surfactant System

The detergent compositions according to the present invention comprise a surfactant system, wherein the surfactant can be selected from nonionic and/or anionic and/or cationic and/or ampholytic and/or zwitterionic and/or semi-polar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present invention comprise as a surfactant one or more of the nonionic and/or anionic surfactants described herein.

Polyethylene, polypropylene, and polybutylene oxide conden-sates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (The condensation product of $C_{11}$-$C_{15}$ linear alcohol with 9 moles ethylene oxide), Tergitol™ 24-L-6 NMW (the condensation product of $C_{12}$-$C_{14}$ primary alcohol with 6 moles ethylene oxide with a narrow molecular weight distribution), both marketed by Union Carbide Corporation; Neodol™ 45-9 (the condensation product of $C_{14}$-$C_{15}$ linear alcohol with 9 moles of ethylene oxide), Neodol™ 23-3 (the condensation product of $C_{12}$-$C_{13}$ linear alcohol with 3.0 moles of ethylene oxide), Neodol™ 45-7 (the condensation product of $C_{14}$-$C_{15}$ linear alcohol with 7 moles of ethylene oxide), Neodol™ 45-5 (the condensation product of $C_{14}$-$C_{15}$ linear alcohol with 5 moles of ethylene oxide) marketed by Shell Chemical Company, Kyro™ EOB (the condensation product of $C_{13}$-$C_{15}$ alcohol with 9 moles ethylene oxide), marketed by The Procter & Gamble Company, and Genapol LA 050 (the condensation product of $C_{12}$-$C_{14}$ alcohol with 5 moles of ethylene oxide) marketed by Hoechst. Preferred range of HLB in these products is from 8-11 and most preferred from 8-10.

Also useful as the nonionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$-$C_{14}$ alkyl phenol ethoxylates having from 3 to 15 ethoxy groups and $C_8$-$C_{18}$ alcohol ethoxylates (preferably $C_{10}$ avg.) having from 2 to 10 ethoxy groups, and mixtures thereof. Highly preferred nonionic surfactants are polyhydroxy fatty acid amide surfactants of the formula:

wherein $R^1$ is H, or $R^1$ is $C_{1-4}$ hydrocarbyl, 2-hydroxyethyl, 2-hydroxypropyl or a mixture thereof. $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula $RO(A)_mSO3M$ wherein R is an unsubstituted $C_{10}$-$C_{24}$ alkyl or hydroxyalkyl group having a $C_{10}$-$C_{24}$ alkyl component, preferably a $C_{12}$-$C_{20}$ alkyl or hydroxyalkyl, more preferably $C_{12}$-$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperidinium cations and those derived from alkylamines such as ethylamine, diethylamine, triethylamine, mixtures thereof, and the like. Exemplary surfactants are $C_{12}$-$C_{18}$ alkyl polyethoxylate (1.0) sulfate ($C_{12}$-$C_{18}$E(10)M), $C_{12}$-$C_{18}$ alkyl polyethoxylate (2.25) sulfate ($C_{12}$-$C_{18}$(2.25)M, and $C_{12}$-$C_{18}$ alkyl polyethoxylate (3.0) sulfate ($C_{12}$-$C_{18}$E(3.0)M), and $C_{12}$-$C_{18}$ alkyl polyethoxylate (4.0) sulfate ($C_{12}$-$C_{18}$E(4.0)M), wherein M is conveniently selected from sodium and potassium.

Suitable anionic surfactants to be used are alkyl ester sulfonate surfactants including linear esters of $C_8$-$C_{20}$ carboxylic acids (i.e., fatty acids) which are sulfonated with gaseous $SO_3$ according to *The Journal of the American Oil Chemists Society* 52: 323-329 (1975). Suitable starting materials would include natural fatty substances as derived from tallow, palm oil, etc.

The preferred alkyl ester sulfonate surfactant, especially for laundry applications, comprises alkyl ester sulfonate surfactants of the structural formula:

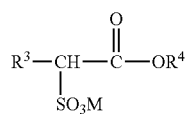

wherein $R^3$ is a $C_8$-$C_{20}$ hydrocarbyl, preferably an alkyl, or combination thereof, $R^4$ is a $C_1$-$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$-$C_{16}$ alkyl, and $R^4$ is methyl, ethyl or isopropyl. Especially preferred are the methyl ester sulfonates wherein $R^3$ is $C_{10}$-$C_{16}$ alkyl.

Other suitable anionic surfactants include the alkyl sulfate surfactants which are water soluble salts or acids of the formula $ROSO_3M$ wherein R preferably is a $C_{10}$-$C_{24}$ hydrocarbyl, preferably an alkyl or hydroxyalkyl having a $C_{10}$-$C_{20}$ alkyl component, more preferably a $C_{12}$-$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations such as tetramethyl-ammonium and dimethyl piperidinium cations and quaternary ammonium cations derived from alkylamines such as ethylamine, diethylamine, triethylamine, and mixtures thereof, and the like). Typically, alkyl chains of $C_{12}$-$C_{16}$ are preferred for lower wash temperatures (e.g., below about 50° C.) and $C_{16}$-$C_{18}$ alkyl chains are preferred for higher wash temperatures (e.g., above about 50° C.).

Other anionic surfactants useful for detersive purposes can also be included in the laundry detergent compositions of the present invention. These can include salts (including, for example, sodium, potassium, ammonium, and substituted ammonium salts such as mono- di- and triethanolamine salts) of soap, $C_8$-$C_{22}$ primary or secondary alkanesulfonates, $C_8$-$C_{24}$ olefinsulfonates, sulfonated polycarboxylic acids prepared by sulfonation of the pyrolyzed product of alkaline earth metal citrates, e.g., as described in British patent specification No. 1,082,179, $C_8$-$C_{24}$ alkylpolyglycolethersulfates (containing up to 10 moles of ethylene oxide); alkyl glycerol sulfonates, fatty acyl glycerol sulfonates, fatty acyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$-$C_{18}$ monoesters) and diesters of sulfosuccinates (especially saturated and unsaturated $C_6$-$C_{12}$ diesters), acyl sarcosinates, sulfates of alkylpolysaccharides such as the sulfates of alkylpolyglucoside (the nonionic non-sulfated compounds being described below), branched primary alkyl sulfates, and alkyl polyethoxy carboxylates such as those of the formula $RO(CH_2CH_2O)_k$—$CH_2COO-M+$ wherein R is a $C_8$-$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vols. I and II by Schwartz, Perry and Berch). A variety of such surfactants are also generally disclosed in U.S. Pat. No. 3,929,678 (column 23, line 58 through column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

[$R^2(OR^3)_y$][$R^4(OR^3)_y$]$_2R^5N+X$— wherein $R^2$ is an alkyl or alkyl benzyl group having from about 8 to about 18 carbon atoms in the alkyl chain, each $R^3$ is selected form the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$-$C_4$ alkyl, $C_1$-$C_4$ hydroxyalkyl, benzyl ring structures formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

$R_1R_2R_3R_4N^+X^-$            (i)

wherein $R_1$ is $C_8$-$C_{16}$ alkyl, each of $R_2$, $R_3$ and $R_4$ is independently $C_1$-$C_4$ alkyl, $C_1$-$C_4$ hydroxy alkyl, benzyl, and —$(C_2H_{40})_xH$ where x has a value from 2 to 5, and X is an anion. Not more than one of $R_2$, $R_3$ or $R_4$ should be benzyl.

The preferred alkyl chain length for $R_1$ is $C_{12}$-$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:
coconut trimethyl ammonium chloride or bromide;
coconut methyl dihydroxyethyl ammonium chloride or bromide;
decyl triethyl ammonium chloride;
decyl dimethyl hydroxyethyl ammonium chloride or bromide;
$C_{12-15}$ dimethyl hydroxyethyl ammonium chloride or bromide;
coconut dimethyl hydroxyethyl ammonium chloride or bromide;
myristyl trimethyl ammonium methyl sulphate;
lauryl dimethyl benzyl ammonium chloride or bromide;
lauryl dimethyl (ethenoxy)$_4$ ammonium chloride or bromide;
choline esters (compounds of formula (I) wherein $R_1$ is

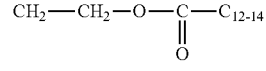

alkyl and $R_2R_3R_4$ are methyl).
di-alkyl imidazolines [compounds of formula (i)].

Other cationic surfactants useful herein are also described in U.S. Pat. No. 4,228,044 and in EP 000224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g., carboxy, sulfonate, sulfate. See U.S. Pat. No. 3,929,678 (column 19, lines 18-35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; watersoluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

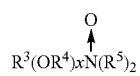

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$-$C_{18}$ alkyl dimethyl amine oxides and $C_8$-$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g., SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2-ethane tetracarboxylates, 1,1,3,3-propane tetracarboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan-cis,cis,cis-tetracarboxylates, 2,5-tetrahydro-furan-cis, discarboxylates, 2,2,5,5-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000-5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the pectate lyase preparation of the invention, comprise other enzyme(s) which provides cleaning performance and/or fabric care benefits. In accordance with the present invention, additional enzymes may be modified in order to improve the oxidation- and calcium-depletion stability.

Such enzymes include proteases, lipases, cutinases, amylases, cellulases, peroxidases, oxidases (e.g., laccases), hemicellulases, such as mannanases, xylanases, galactanases, arabinofuranosidases, esterases, lichenases, arabinanases and other pectate lyases.

Proteases:

Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270.

Preferred commercially available protease enzymes include those sold under the trade names Alcalase, Savinase, Primase, Durazym, and Esperase by Novo Nordisk NS (Denmark), those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases:

Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258068 and EP 305216, a *Rhizomucor miehei* lipase, e.g., as described in EP 238023, a *Candida* lipase, such as a *C. antarctica* lipase, e.g., the *C. antarctica* lipase A or B described in EP 214761, a *Pseudomonas lipase* such as a *P. alcaligenes* and *P. pseudoalcaligenes* lipase, e.g., as described in EP 218272, a *P. cepacia* lipase, e.g., as described in EP 331376, a *P. stutzeri* lipase, e.g., as disclosed in GB 1,372,034, a *P. fluorescens* lipase, a *Bacillus* lipase, e.g., a *B. subtilis* lipase (Dartois et al., 1993, *Biochemica et Biophysica Acta* 1131: 253-260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., 1991, *Gene* 103: 61-67), the *Geotricum candidum* lipase (Schimada et al., 1989, *J. Biochem.* 106: 383-388), and various *Rhizopus* lipases such as a *R. delemar* lipase (Hass et al., 1991, *Gene* 109: 117-113), a *R. niveus* lipase (Kugimiya et al., 1992, *Biosci. Biotech. Biochem.* 56: 716-719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g., described in WO 90/09446).

Especially suitable lipases are lipases such as M1 Lipase™, Luma Fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases:

Any amylase (alpha and/or beta) suitable for use in alkaline solutions can be used. Suitable amylases include those of bacterial or fungal origin. Chemically or genetically modified mutants are included. Amylases include, for example, alpha-amylases obtained from a special strain of *B. licheniformis*, described in more detail in GB 1,296,839. Commercially available amylases are Duramyl™, Termamyl™, Fungamyl™ and BAN™ (available from Novo Nordisk A/S) and Rapidase™, Maxamyl P™, Purastar™ and Purastar OxAm™ (available from Genencor). Further, an amylase with more than 70% homology to SP707 (Tsukamoto et al., 1988, *Biochem. Biophys. Res. Commun.* 151:25) or K38 (Kao Corp. EP 1022334) is suitable.

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases:

Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307, which discloses fungal cellulases produced from *Humicola insolens*. Especially suitable cellulases are the cellulases having colour care benefits. Examples of such cellulases are cellulases described in European patent application No. 0 495 257.

Commercially available cellulases include Celluzyme™ produced by a strain of *Humicola insolens* (Novo Nordisk A/S), and KAC-500(B)™ (Kao Corporation).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases:

Peroxidase enzymes are used in combination with hydrogen peroxide or a source thereof (e.g., a percarbonate, perborate or persulfate). Oxidase enzymes are used in combination with oxygen. Both types of enzymes are used for "solution bleaching", i.e., to prevent transfer of a textile dye from a dyed fabric to another fabric when said fabrics are washed together in a wash liquor, preferably together with an enhancing agent as described in, e.g., WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Pectate Lyases:

Pectate lyases have been cloned from different bacterial genera such as *Erwinia*, *Pseudomonas*, *Klebsiella* and *Xanthomonas*. Also from *Bacillus subtilis* (Nasser et al., 1993, *FEBS* 335:319-326) and *Bacillus* sp. YA-14 (Kim et al., 1994, *Biosci. Biotech. Biochem.* 58:947-949) cloning of a pectate lyase has been described.

The pectate lyases are generally characterised by an alkaline pH optimum and an absolute requirement for divalent cations, $Ca^{2+}$ being the most stimulatory.

Mixtures of the above mentioned enzymes are encompassed herein, in particular a mixture of a protease, an amylase, a lipase and/or a cellulase.

The pectate lyase of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching Agents:

Additional optional detergent ingredients that can be included in the detergent compositions of the present invention include bleaching agents such as PB1, PB4 and percarbonate with a particle size of 400-800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g., granular detergents.

The bleaching agent component for use herein can be any of the bleaching agents useful for detergent compositions including oxygen bleaches as well as others known in the art. The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. Nos. 4,483,781, 4,740,446, and 4,412,934 and EP 133354. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5-10% by weight of the finished product, preferably 1-5% by weight.

The hydrogen peroxide releasing agents can be used in combination with bleach activators such as tetra-acetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzene-sulfonate and C10 (6-decanamido caproyl) oxybenzene-sulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. application Ser. No. 08/136,626.

The hydrogen peroxide may also be present by adding an enzymatic system (i.e., an enzyme and a substrate therefore) which is capable of generation of hydrogen peroxide at the beginning or during the washing and/or rinsing process. Such enzymatic systems are disclosed in EP 537381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", *Nature* 369: 637-639 (1994).

Suds Suppressors:

Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanols which are commercially available under the trade name Isofol 12 R.

Such suds suppressor system are described in European Patent Application EP 593841.

Especially preferred silicone suds controlling agents are described in European Application No. 92201649.8. Said compositions can comprise a silicone/silica mixture in combination with fumed nonporous silica such as Aerosil$^R$.

The suds suppressors described above are normally employed at levels of from 0.001% to 2% by weight of the composition, preferably from 0.01% to 1% by weight.

Other Components:

Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2'-disulphonate, disodium 4,4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-triazin-6-ylamino) stilbene-2-sulphonate, disodium 4,4'-bis-(2-anilino-4-(N-methyl-N-2-hydroxyethylamino)-s-triazin-6-ylamino)stilbene-2,2'-disulphonate, disodium 4,4'-bis-(4-phenyl-2,1,3-triazol-2-yl)-stilbene-2,2'-disulphonate, disodium 4,4'-bis(2-anilino-4-(1-methyl-2-hydroxyethylamino)-s-triazin-6-ylamino)stilbene-2,2'disulphonate, sodium 2-(stilbyl-4"-(naphtho-1',2':4,5)-1,2,3-triazole-2"-sulphonate and 4,4'-bis (2-sulphostyryl)biphenyl.

Other useful polymeric materials are the polyethylene glycols, particularly those of molecular weight 1000-10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 272033. A particular preferred polymer in accordance with EP 272033 has the formula:

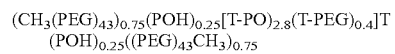

where PEG is —(OC$_2$H$_4$)O—, PO is (OC$_3$H$_6$O) and T is (pOOC$_6$H$_4$CO).

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311342.

Softening Agents:

Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019, 292. Organic fabric softening agents include the water insoluble tertiary amines as disclosed in GB-A1 514 276 and EP 011340 and their combination with mono C$_{12}$-C$_{14}$ quaternary ammonium salts are disclosed in EP 026528 and dilongchain amides as disclosed in EP 242919. Other useful organic ingredients of fabric softening systems include high molecular weight polyethylene oxide materials as disclosed in EP 299575 and 313146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric Dye-Transfer Inhibiting Agents:

The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e., they may have a relatively higher density than conventional granular detergents, i.e., form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention.

In the detergent compositions, the abbreviated component identifications have the following meanings:

LAS: Sodium linear $C_{12}$ alkyl benzene sulfonate
TAS: Sodium tallow alkyl sulfate
XYAS: Sodium $C_{1X}$-$C_{1Y}$ alkyl sulfate
SS: Secondary soap surfactant of formula 2-butyl octanoic acid
25EY: A $C_{12}$-$C_{15}$ predominantly linear primary alcohol condensed with an average of Y moles of ethylene oxide
45EY: A $C_{14}$-$C_{15}$ predominantly linear primary alcohol condensed with an average of Y moles of ethylene oxide
XYEZS: $C_{1X}$-$C_{1Y}$ sodium alkyl sulfate condensed with an average of Z moles of ethylene oxide per mole
Nonionic: $C_{13}$-$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh
CFAA: $C_{12}$-$C_{14}$ alkyl N-methyl glucamide
TFAA: $C_{16}$-$C_{18}$ alkyl N-methyl glucamide
Silicate: Amorphous Sodium Silicate ($SiO_2$:$Na_2O$ ratio=2.0)
NaSKS-6: Crystalline layered silicate of formula $\delta$-$Na_2Si_2O_5$
Carbonate: Anhydrous sodium carbonate
Phosphate: Sodium tripolyphosphate
MA/AA: Copolymer of 1:4 maleic/acrylic acid, average molecular weight about 80,000
Polyacrylate: Polyacrylate homopolymer with an average molecular weight of 8,000 sold under the tradename PA30 by BASF Gmbh
Zeolite A: Hydrated Sodium Aluminosilicate of formula $Na_{12}$($AlO_2SiO_2$)$_{12}$·$27H_2O$ having a primary particle size in the range from 1 to 10 micrometers
Citrate: Tri-sodium citrate dihydrate
Citric: Citric Acid
Perborate: Anhydrous sodium perborate monohydrate bleach, empirical formula $NaBO_2.H_2O_2$
PB4: Anhydrous sodium perborate tetrahydrate
Percarbonate: Anhydrous sodium percarbonate bleach of empirical formula $2Na_2CO_3.3H_2O_2$
TAED: Tetraacetyl ethylene diamine
CMC: Sodium carboxymethyl cellulose
DETPMP: Diethylene triamine penta (methylene phosphonic acid), marketed by Monsanto under the Tradename Dequest 2060
PVP: Polyvinylpyrrolidone polymer
EDDS: Ethylenediamine-N,N'-disuccinic acid, [S,S] isomer in the form of the sodium salt
Suds 25% paraffin wax Mpt 50° C., 17% hydrophobic silica, 58%
Suppressor: paraffin oil
Granular Suds 12% Silicone/silica, 18% stearyl alcohol, 70% suppressor: starch in granular form
Sulphate: Anhydrous sodium sulphate
HMWPEO: High molecular weight polyethylene oxide
TAE 25: Tallow alcohol ethoxylate (25)

DETERGENT EXAMPLE I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

DETERGENT EXAMPLE II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS- | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

DETERGENT EXAMPLE III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

DETERGENT EXAMPLE IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

DETERGENT EXAMPLE V

Heavy duty liquid fabric cleaning compositions in accordance with the invention may be prepared as follows:

| | A | B |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5.0 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl-hydroxy ethyl ammonium chloride | — | 3.0 |
| Smectite clay | — | 5.0 |
| PVP | 2.0 | — |
| Water/Minors | Up to 100% | |

EXAMPLE 1

Measuring the Stability of Pectate Lyase in Liquid Detergent

The detergent stability of the pectate lyase variants of the present invention is assessed by measuring the activity of the variants after incubation of an enzyme-detergent mixture, which is described below.

Residual Activity Assay:

30 microliters of an enzyme solution (culture supernatant or purified enzyme) is mixed with 1 ml of typical European or US heavy duty liquid detergent in two sample tubes. One of the tubes is stored on ice while the other is incubated at 40° C. for 90 minutes. As reference 30 microliters water is mixed with 1 ml of detergent and incubated on ice.

After incubation, 9 ml of ice-cold water is added to the samples, which are mixed vigorously and stored on ice until further analysis.

The enzymatic activity is measured by first mixing 50 microliters of enzyme-detergent mixture with 5 ml of assay buffer (100 mM Tris-HCL, 0.68 mM $CaCl_2$, pH 8.0), secondly from which solution, 75 microliters is mixed with 75 microliters freshly prepared substrate solution (1% polygalactoronic acid in assay buffer) and incubated at 40° C. for 10 minutes. Thirdly, 100 microliters of the incubation mixture is added into 100 microliters stop-buffer (50 mM $H_3PO_4$) in a UV-transparent microtiterplate and the absorbance at 235 nm is measured in a spectofotometer. The water-detergent sample is used to zero the spectofotometer.

Now the residual activity is calculated as the activity (A235 absorbance) in the sample incubated at 40° C. for 90 minutes relative to the activity in the sample stored on ice:

Residual activity(RA)=Absorbance[sample incubated at 40° C.]/Absorbance[sample incubated at 0° C.]×100

Thus the residual activity is equivalent to the detergent stability of the enzyme. Table 2 lists the improved residual activity of a number of substitutions of the pectate lyase of SEQ ID NO: 2 incubated in a typical European heavy duty liquid detergent. The majority of the substitutions give rise to more than 50% improvement of the detergent stability compared to the parent pectate lyase as shown in SEQ ID NO: 2. Equivalently the substitutions of the pectate lyase of SEQ ID NO: 2 listed in Table 3 significantly improve the stability of the enzyme when incubated in a typical US heavy duty liquid detergent.

TABLE 2

Substitutions in the pectate lyase of SEQ ID NO: 2 giving rise to increased residual activity after incubation in European heavy duty liquid detergent.

| Mutations | Residual activity % | Residual activity in % of parent enzyme |
|---|---|---|
| Pectate lyase of SEQ ID NO: 2 (parent enzyme) | 23 | 100 |
| Q40E | 28 | 122 |
| F251I | 30 | 130.4 |
| A332P | 31 | 134.8 |
| L106Q | 31 | 134.8 |
| R272H | 31 | 134.8 |
| R272Y | 31 | 134.8 |
| A91E | 33 | 143.5 |
| K115I + K213E | 33 | 143.5 |
| K139I + K213N | 33 | 143.5 |
| H5R + K257N + S302A | 34 | 147.8 |
| K139M | 34 | 147.8 |
| K87A | 34 | 147.8 |
| D48P | 35 | 152.2 |
| K99I + I196V | 35 | 152.2 |
| T105P | 35 | 152.2 |
| K115A + K118A | 36 | 156.5 |
| K115A + K118A + M122N | 36 | 156.5 |
| K115Q | 36 | 156.5 |
| K213T | 36 | 156.5 |
| V141E + C199S + K213E | 36 | 156.5 |
| K115I + Q146H | 37 | 160.9 |
| K257N | 37 | 160.9 |
| K71E + K118E | 38 | 165.2 |
| S331P | 38 | 165.2 |
| T49P + N156S | 38 | 165.2 |
| K314N + S340P | 39 | 169.6 |
| V141E + I235V | 39 | 169.6 |
| G46D + K257N | 40 | 173.9 |
| Q146H | 40 | 173.9 |
| K218P | 41 | 178 |
| A305P | 41 | 178 |
| S28T + S30F + K334E + N363S | 41 | 178 |
| H193Y + S256C + V389I + A393V | 42 | 183 |
| R272C | 42 | 183 |
| D48E + L106Q + I140V + F215Y + K218E | 42 | 183 |
| K213N + T258I | 43 | 187 |
| E9G + H31N + N50D + L106Q + A111E + T136S + V141L + F201L + N202K + F215Y + G286A + A381D + H384N | 43 | 187 |

TABLE 2-continued

Substitutions in the pectate lyase of SEQ ID NO: 2 giving rise to increased residual activity after incubation in European heavy duty liquid detergent.

| Mutations | Residual activity % | Residual activity in % of parent enzyme |
|---|---|---|
| E9G + H31N + L106Q + D303S + A305P + T335S + H384N + S391N | 44 | 191 |
| E9G + H31N + D48E + L106Q + A111E + S301Y + D303S + A305P + T378S + H384N + S391N | 45 | 196 |
| L45V + N50Y + N185H | 46 | 200 |
| N11Y + K87E + K99N | 46 | 200 |
| K115I + K213E | 48 | 209 |
| E9G + D48E + L106Q + S316F + A381D | 48 | 209 |
| S30P + K115I + K139I + Q146H + S337C | 49 | 213 |
| K213N + T258I | 50 | 217 |
| K47R + K257N | 50 | 217 |
| E9G + H31N + D48E + L106Q + I140V + F215Y + D303S + A305P + T378S + H384N + S391N | 51 | 222 |
| H31N + T105A + L106Q + A111E + V141L + K218E + D303S + A305P + D326N + T335S + H384N + S391N | 51 | 222 |
| E9G + L106Q + I140V + G204R + F215Y + D303S + A305P + T378S + H384N + S391N | 52 | 226 |
| K26Q + K47N + L106Q + I140V + F215Y + D303S + A305P + T378S + H384N + S391N | 53 | 230 |
| D48E + L106Q + I140V + F215Y + D303S + A305P + T378S + H384N + S391N | 56 | 243 |
| D48E + L106Q + K213T + F215Y + K218L + A305P | 57 | 248 |
| L106Q + S337C | 57 | 248 |
| K115I + K213N | 57 | 248 |
| E9G + H31N + T61A + G74D + L75A + N76D + K79A + D86N + E107K + T136S + V141L + F215Y + K218E + V324A + A333E + S340K + G341S + T378S + H384N + S391N | 57 | 248 |
| T52M + K139I + Q146H + I196V + K213N + K257N + T258I + N323M + S366N | 57 | 248 |
| T51Y + I186H + K213N + K257N | 59 | 257 |
| K213N | 60 | 261 |
| K139I + Q146H + K213N + T258I + S337C | 60 | 261 |
| E9G + D48E + G74D + L75A + N76D + K79A + D86N + L106Q + T136S + V141L + K148E + I194V + G204R + F215Y + D303S + A305P + T378S + H384N + S391N | 61 | 265 |
| H31N + D48E + L106Q + T136S + V141L + I194V + S331T + H384N + K386R + S387A + I390T | 62 | 270 |
| K213T + K218L + A305P | 64 | 278 |
| S337C | 65 | 283 |
| M122Q + K115Q + K118Q + K139I + Q146H + S337C | 66 | 287 |
| M64F + K213T + K218P + A305P | 66 | 287 |
| K213T + K218P + A305P + D48P + T105P + K139I + T258I | 67 | 291 |
| L45V + K139I + Q146H + N185H + I196V + S337C + G377E + S387I | 67 | 291 |
| M64F + L106Q + K213T + F215Y + K218L + A305P | 68 | 296 |
| M64F + K213T + K218L + A305P | 70 | 304 |
| M64F + M122K + K118E + K213T + K218L + A305P | 71 | 309 |
| K213T + K218P + A305P + D48P + T105P + K139T | 71 | 309 |
| D48E + M64F + L106Q + M122K + K118E + K213T + F215Y + K218L + A305P | 72 | 313 |
| L45V + K139N + Q146H + I196V + T258I | 72 | 313 |
| K139I + V141G + Q146H + S337C + I357V | 72 | 313 |
| K99I + K139I + Q146H + N185H + I196V + K213N + K257N + T258I | 73 | 317 |
| K139I + Q146H + S337C | 74 | 322 |
| M64F + M122K + K118E + Q146H + K213T + K218L + A305P + S340Q | 74 | 322 |
| M122K + K118E + K139I + Q146H + S337C | 75 | 326 |
| K139N + E158N + Q146H + S337C | 75 | 326 |
| M64F + K118E + M122K + Q146H + K213N + K218P + A305P | 75 | 326 |
| K139I; Q146H + K257N + S337C | 75 | 326 |
| K99I + I196V + K213N | 75 | 326 |
| K139I + Q146H + R272C | 75 | 326 |
| K139I + Q146H + N323M + S337C | 75.5 | 328 |
| M64F + M122K + K118E + Q146H ++ I196V + K218L + A305P | 76 | 330 |
| L45V + N116D + N185H + K257N + T258I + S337C + Q356H | 76 | 330 |
| M64F + M237I + K139I + Q146H + S337C | 77 | 335 |
| D48P + M64F + K213T + K218L + A305P + S331P | 77 | 335 |
| M64F + K139N + Q146H + E158N + S337C | 77 | 335 |
| K139I + Q146H + S337C | 77 | 335 |
| M64F + M122E + K139I + Q146H + S337C | 78 | 339 |
| M64F + M122K + K118E + K139I + Q146H + S337C | 78 | 339 |
| D48P + T105P + K139N + K213N + K218P + T258N + A305P + S331P | 78 | 339 |
| M64F + K139S + Q146H + S337C | 78 | 339 |
| M64F + M122K + K118E + Q146H + K213T + K218L + A305P | 79 | 343 |
| K139I + Q146H + K213N + S331P + S337C | 80 | 348 |
| Q146H + V338E | 81 | 352 |
| K139I + Q146H + N189D + S337R | 81 | 352 |
| M64F + K139H + Q146H + S337C | 81 | 352 |
| K139I + S337C + S340N | 81.5 | 354 |

TABLE 2-continued

Substitutions in the pectate lyase of SEQ ID NO: 2 giving rise to increased residual activity after incubation in European heavy duty liquid detergent.

| Mutations | Residual activity % | Residual activity in % of parent enzyme |
|---|---|---|
| M64F + L106Q + K139I + Q146H + K213T + K218L + A305P + S337C | 82 | 357 |
| N76D + K139I + Q146I + S337C | 82 | 357 |
| M64F + K139F + Q146V + S337C | 82 | 357 |
| M64F + K139I + Q146H + Y308S + T335R + I336S + S337L + V338Y + F339I + S340A | 82 | 357 |
| D48P + M64F + T105P + K139N + Q146H + K213N + K218P + T258N + A305P + S331P | 83 | 361 |
| M64F + V123I + K139I + Q146H + S337C | 84 | 365 |
| M64F + M122K + K118E + Q146H + K213T + K218L + A305P + S337C | 84 | 365 |
| K139I + Q146H + S256C | 84 | 365 |
| N37D + K139I + Q146H + K213E + S307R + S337C | 84 | 365 |
| K139I + Q146H + S229T + S337C | 84 | 365 |
| M64F + K139S + Q146V + S337C | 84 | 365 |
| M64F + M122V + K139Q + Q146L + S337C + K397D | 84 | 365 |
| M64F + K139I + Q146V + S337C | 84 | 365 |
| D48P + M64F + K118E + M122K + Q146H + D170N + K213N + K218P + A305P + S331P | 85 | 370 |
| L45V + K213N + K257N + S337C + T378G + H384N + S391N | 85 | 370 |
| M64F + M122K + K118E + Q146H + K213T + K218L + A305P + S340P | 86 | 374 |
| K139I + V141G + Q146H + V277D | 86 | 374 |
| M64F + K139L + Q146F + S337C | 86 | 374 |
| M64F + K99I + T105P + M122K + K118E + Q146H + K213N + K218P + A305P + S331P | 86.5 | 376 |
| K213T + K218P + A305P + D48P + T105P + K139I + T258I + S331P | 87 | 378 |
| D48P + M64F + T105P + K139N + Q146H + K213T + K218P + T258I + A305P + S331P | 89 | 387 |
| M64F + K139I + Q146H + S337C | 90 | 391 |
| D48P + M64F + T105P + K139I + Q146H + K213T + K218P + T258I + A305P + S331P | 90.5 | 393 |
| M64F + K139I + Q146H + K213T + K218L + A305P + S337C | 91 | 396 |
| D48P + T105P + K139N + K213T + K218P + T258I + A305P + S331P | 91 | 396 |
| M64F + M122K + K118E + Q146H + K213T + K218L + A305P + S337K | 91 | 396 |
| D48P + M64F + T105P + K139I + Q146H + K213T + K218P + T258I + A305P + S331P | 91 | 396 |
| V141E + C199S + K213E + Y295H | 91 | 396 |
| D48P + M64F + T105P + M122K + K118E + K213T + K218P + A305P + S331P | 92 | 400 |
| D48P + M64F + K139I + Q146H + K213T + K218L + A305P + S337K | 92 | 400 |
| D48P + T105P + K139N + K213T + K218P + T258I + A305P + S331P + S337R | 92 | 400 |
| D48P + M64F + T105P + K139I + Q146H + K213T + K218P + T258I + A305P + S331P + S337K | 92 | 400 |
| D48P + M64F + L106Q + K139I + Q146H + K213T + K218L + A305P + S337C | 93 | 404 |
| D48P + M64F + T105P + K139I + Q146H + K148E + K213T + K218P + T258I + A305P + S331P + S337R | 93 | 404 |
| M64F + L75P + K139E + Q146V + G224S + S337C + G349R + V389I | 93 | 404 |
| M64F + K139I + Q146H + K213T + K218L + A305P + T258P + S331P + S337C | 94 | 409 |
| D48P + M64F + L106Q + K139I + Q146H + K213T + K218L + Y234H + A305P + S331P + S337C | 94 | 409 |
| M64F + M122K + K118E + Q146H + K213T + K218L + A305P + S337R | 97 | 422 |
| D48P + T105P + K139N + K213T + K218P + T258I + A305P + S331P + S337K | 97 | 422 |
| D48P + M64F + T105P + K139I + Q146H + K213T + K218P + T258I + A305P + S331P + S340P | 97 | 422 |
| M64F + K139I + Q146H + K213T + K218L + A305P + S331P + S337C | 98 | 426 |
| D48P + M64F + K139I + Q146H + K213T + K218L + A305P + S337C | 98 | 426 |
| D48P + M64F + K139I + Q146H + K213T + K218L + A305P + S337R | 98 | 426 |
| D48P + M64F + T105P + K139I + Q146H + K213T + K218P + T258I + A305P + S331P + S337R | 99 | 430 |
| D48P + M64F + T105P + K139I + Q146H + N189D + K213T + K218P + T258I + S298N + A305P + S331P + S337R | 100 | 435 |
| D48P + M64F + T105P + K139I + Q146H + K213T + K218P + T258I + A305P + S331P + S337K + S340P | 100 | 435 |
| D48P + M64F + T105P + K139I + Q146H + K213T + K218P + T258I + A305P + S331P + K334E + S337K + S340P | 100 | 435 |

TABLE 3

Substitutions in the pectate lyase of SEQ ID NO: 2 giving rise to increased residual activity after incubation in US heavy duty liquid detergent.

| Mutations | Residual activity % | Residual activity in % of parent enzyme |
|---|---|---|
| Pectate lyase of SEQ ID NO: 2 (parent enzyme) | 45 | 100 |
| D68* + N69* + L70* + K71* | 46 | 102 |
| N50L + K54V | 46 | 102 |
| I390N | 46 | 102 |
| V141N | 47 | 104 |
| L75P | 47 | 104 |
| K115N | 47 | 104 |
| L268Y + F251I | 48 | 107 |
| A91E | 48 | 107 |
| T105P | 48 | 107 |
| L106Q | 49 | 109 |
| K87A | 49 | 109 |
| S30T + K99I | 49 | 109 |
| K139I + K213N | 49 | 109 |
| R272Y | 50 | 111 |
| M237I | 51 | 113 |
| C199N | 51 | 113 |
| F215Y | 52 | 116 |
| K213T | 52 | 116 |
| A228I + F251I | 53 | 118 |
| K115I + Q146H | 57 | 127 |
| K257N | 59 | 131 |
| K213N + T258I | 60 | 133 |
| M122Q | 61 | 136 |
| K386P | 61 | 136 |
| K218P | 61 | 136 |
| A332P | 62 | 138 |
| F251I | 64 | 142 |
| A305P | 64 | 142 |
| D48P | 64 | 142 |
| S134L + K257E | 66 | 147 |
| M64F + K213T + K218L + A305P | 73 | 162 |
| S331P | 75 | 167 |
| M64F + M122K + K118E + K213T + K218L + A305P | 78 | 173 |
| M64F + K139I + Q146H + S337C | 91 | 202 |
| M64F + V123I + K139I + Q146H + S337C | 91 | 202 |
| K139I + Q146H + S337C | 100 | 222 |

EXAMPLE 2

Stability of Pectate Lyases in Liquid Detergent after Prolonged Incubation

The detergent stability of the pectate lyase variants of the present invention is assessed by measuring the activity of the variants after incubation of an enzyme-detergent mixture, which is described below.

Residual Activity Assay:

30 microliters of an enzyme solution (culture supernatant or purified enzyme) is mixed with 1 ml of typical European heavy duty liquid detergent in two sample tubes. One of the tubes is stored on ice while the other is incubated at 40° C. for 18 or 24 hours. As reference 30 microliters water is mixed with 1 ml of detergent and incubated on ice.

After incubation, 9 ml of ice-cold water is added to the samples, which are mixed vigorously and stored on ice until further analysis.

The enzymatic activity is measured by first mixing 50 microliters of enzyme-detergent mixture with 5 ml of assay buffer (100 mM Tris-HCL, 0.68 mM $CaCl_2$, pH 8.0), secondly from which solution, 75 microliters is mixed with 75 microliters freshly prepared substrate solution (1% polygalactoronic acid in assay buffer) and incubated at 40° C. for 10 minutes. Thirdly, 100 microliters of the incubation mixture is added into 100 microliters stop-buffer (50 mM $H_3PO_4$) in a UV-transparent microtiterplate and the absorbance at 235 nm is measured in a spectofotometer. The water-detergent sample is used to zero the spectofotometer.

Now the residual activity is calculated as the activity (A235 absorbance) in the sample incubated at 40° C. for 90 minutes relative to the activity in the sample stored on ice:

Residual activity(RA)=Absorbance[sample incubated at 40° C.]/Absorbance[sample incubated at 0° C.]×100

Thus the residual activity is equivalent to the detergent stability of the enzyme. Table 4 lists the improved residual activity of a number of substitutions of the pectate lyase of SEQ ID NO: 2 incubated in a typical European heavy duty liquid detergent for 18 hours. Likewise Table 5 lists the residual activity of pectate lyase variants incubated for 24 hours.

TABLE 4

Substitutions in the pectate lyase of SEQ ID NO: 2 giving rise to increased residual activity, which is measured after incubation in European heavy duty liquid detergent for 18 hours.

| Mutations | Residual activity % |
|---|---|
| Pectate lyase of SEQ ID NO: 2 (parent enzyme) | <5% |
| K139I + Q146H + S337C | 22 |
| D48P + M64F + K139I + Q146H + K213T + K218L + A305P + S337C | 53 |
| D48P + M64F + T105P + M122K + K118E + K213T + K218P + A305P + S331P | 41 |
| M64F + M122K + K118E + Q146H + K213T + K218L + A305P + S340P | 38 |
| D48P + M64F + T105P + K139I + Q146H + K213T + K218P + T258I + A305P + S331P | 37 |
| D48P + M64F + K99I + K118E + M122K + Q146H + K213N + K218P + A305P + S331P | 24 |
| D48P + T105P + K139N + K213T + K218P + T258I + A305P + S331P | 23 |
| D48P + M64F + K139I + Q146H + K213T + K218L + A305P + S337K | 56 |
| D48P + M64F + K139I + Q146H + K213T + K218L + A305P + S337R | 46 |
| M64F + M122K + K118E + Q146H + K213T + K218L + A305P + S337K | 49 |
| M64F + M122K + K118E + Q146H + K213T + K218L + A305P + S337R | 59 |
| D48P + T105P + K139N + K213T + K218P + T258I + A305P + S331P + S337K | 60 |
| D48P + T105P + K139N + K213T + K218P + T258I + A305P + S331P + S337R | 57 |
| D48P + M64F + T105P + K139N + Q146H + K213T + K218P + T258I + A305P + S331P | 32 |
| D48P + K99I + T105P + K139N + K213T + K218P + T258I + A305P + S331P | 44 |
| D48P + M64F + L106Q + K139I + Q146H + K213T + K218L + Y234H + A305P + S331P + S337C | 52 |

TABLE 4-continued

Substitutions in the pectate lyase of SEQ ID NO: 2 giving rise to increased residual activity,
which is measured after incubation in European heavy duty liquid detergent for 18 hours.

| Mutations | Residual activity % |
|---|---|
| D48P + M64F + T105P + K139I + Q146H + K213T + K218P + T258I + A305P + S331P + S337R | 80 |
| D48P + M64F + T105P + K139I + Q146H + K213T + K218P + T258I + A305P + S331P + S340P | 64 |
| D48P + M64F + T105P + K139N + Q146H + K213T + K218P + T258I + A305P + S331P | 30 |
| D48P + M64F + T105P + K139I + Q146H + N189D + K213T + K218P + T258I + A305P + S331P + S337R | 80 |
| D48P + M64F + T105P + K139I + Q146H + K213T + K218P + T258I + A305P + S331P | 32 |

TABLE 5

Substitutions in the pectate lyase of SEQ ID NO: 2 giving rise to increased residual activity,
which is measured after incubation in European heavy duty liquid detergent for 24 hours.

| Mutations | Residual Activity % |
|---|---|
| Pectate lyase of SEQ ID NO: 2 (parent enzyme) | <5 |
| D48P + M64F + T105P + K139I + Q146H + K213T + K218P + T258I + A305P + S331P + S337R | 67 |
| D48P + M64F + T105P + K139I + Q146H + K213T + K218P + T258I + A305P + S331P + S337K + S340P | 85 |
| D48P + M64F + T105P + K139I + Q146H + N189D + K213T + K218P + T258I + S298N + A305P + S331P + S337R | 77 |
| D48P + M64F + T105P + K139I + Q146H + K148E + K213T + K218P + T258I + A305P + S331P + S337R | 77 |
| D48P + M64F + T105P + K139I + Q146H + K213T + K218P + T258I + A305P + S331P + K334E + S340P | 60 |
| D48P + M64F + T105P + K139I + Q146H + K213T + K218P + T258I + A305P + S331P + K334E + S337K + S340P | 90 |
| D48P + M64F + T105P + K139N + K213T + K218P + T258I + A305P + S331P + S337K | 69 |
| D48P + M64F + T105P + K139N + K213T + K218P + T258I + A305P + S331P + S337R | 63 |
| D48P + M64F + T105P + K139I + Q146H + K213T + K218P + T258I + A305P + S331P + S337K | 80 |
| D48P + M64F + T105P + K139I + Q146H + K148Q + K213T + K218P + T258I + A305P + S331P + S337K | 83 |
| D48P + M64F + T105P + K139I + V141E + Q146H + K213T + K218P + T258I + A305P + S331P + S337K | 88 |
| D48P + M64F + T105P + K139I + Q146H + C199S + K213T + K218P + T258I + A305P + S331P + S337K | 82 |
| D48P + M64F + T105P + K139I + Q146H + K213T + K218P + T258I + Y295H + A305P + S331P + S337K | 84 |
| D48P + M64F + T105P + K139I + Q146H + K213T + K218P + T258I + A305P + S331P + K334E + S337K | 86 |
| D48P + M64F + K99R + T105P + K139I + Q146H + K213T + K218P + T258I + A305P + S331P + S337K | 82 |

EXAMPLE 3

DSC on Pectate Lyase Wild-Types and Variants

The thermal stability of pectate lyase variants of the invention was measured with differential scanning calorimetry (DSC). The experiments were conducted in a buffer (as opposed to detergent). Purified enzyme samples were dialysed twice against 5 L 20 mM HEPES buffer, 0.68 mM CaCl$_2$, pH 8.0 in 10 kDa cut-off Slide-A-Lyzers (Pierce, USA) and concentrated to approx. 10 mg/ml by 2,400 g centrifugation in a Biofuge Stratos (Kendro, Germany) in YM 10 kDa Centricon cells (Amicon). DSC was run in a MCS 4100 (calorimetry Sciences Corporation, USA) with a 1° C./min gradient from 5 to 110° C. and data analysed by CpCalc 2.1 software (Applied Thermodynamics, USA).

TABLE 6

Transition temperatures ($T_t$) for the tested pectate lyase enzymes.

| Mutations | $T_t$ (° C.) |
|---|---|
| Parent | 67.6 |
| D48P + M64F + T105P + K139I + Q146H + K213T + K218P + T258I + A305P + S331P | 71.5 |
| K139I + Q146H + S337C | 72.4 |
| D48P + M64F + T105P + K139I + Q146H + K213T + K218P + T258I + A305P + S331P + S340P | 74.1 |
| D48P + M64F + T105P + K139I + Q146H + K213T + K218P + T258I + A305P + S331P + K334E + S337K + S340P | 74.2 |

TABLE 6-continued

Transition temperatures (T_t) for the tested pectate lyase enzymes.

| Mutations | $T_t$ (° C.) |
|---|---|
| M64F + K139I + Q146H + S337C | 74.5 |
| D48P + M64F + T105P + K139I + Q146H + N189D + K213T + K218P + T258I + S298N + A305P + S331P + S337R | 74.7 |
| D48P + M64F + T105P + K139I + Q146H + K213T + K218P + T258I + A305P + S331P + S337K | 75.0 |
| D48P + M64F + T105P + K139I + Q146H + K213T + K218P + T258I + A305P + S331P + S337R | 75.6 |
| D48P + M64F + T105P + K139I + Q146H + K148E + K213T + K218P + T258I + A305P + S331P + S337R | 76.6 |
| D48P + M64F + T105P + K139I + Q146H + K213T + K218P + T258I + A305P + S331P + S337K + S340P | 77.7 |

It is noted that that all variants are thermally stabilized compared to the parent.

The invention claimed is:

1. A pectate lyase variant having pectate lyase activity (EC 4.2.2.2) and comprising an alteration at one or more positions selected from the group consisting of positions numbered: 5, 11, 26, 28, 30, 37, 40, 45, 46, 47, 49, 50, 51, 52, 54, 61, 64, 68, 69, 70, 71, 74, 75, 76, 79, 86, 87, 91, 99, 105, 107, 111, 115, 116, 118, 122, 123, 134, 136, 139, 141, 146, 148, 156, 158, 170, 182, 185, 186, 189, 193, 194, 196, 199, 201, 202, 204, 213, 218, 224, 228, 229, 234, 235, 237, 251, 256, 257, 258, 272, 277, 286, 295, 298, 301, 302, 303, 308, 314, 316, 323, 324, 326, 331, 332, 333, 334, 335, 336, 337, 338, 339, 340, 341, 349, 356, 357, 363, 366, 381, 384, 386, 387, 389, 390, 393 and 397 wherein the alteration(s) are independently
(i) an insertion of an amino acid downstream of the amino acid which occupies the position,
(ii) a deletion of the amino acid which occupies the position, or
(iii) a substitution of the amino acid which occupies the position with a different amino acid,
and wherein each position corresponds to a position of the amino acid sequence of the pectate lyase having the amino acid sequence of SEQ ID NO:2,
and wherein the variant pectate lyase has at least 70% identity to the amino acid sequence of SEQ ID NO:2.

2. The variant pectate lyase according to claim 1 which has a degree of identity to the amino acid sequence of SEQ ID NO:2 of at least 80%.

3. The variant pectate lyase according to claim 1 which has a degree of identity to the amino acid sequence of SEQ ID NO:2 of at least 90%.

4. The variant pectate lyase according to claim 1 which has a degree of identity to the amino acid sequence of SEQ ID NO:2 of at least 95%.

5. The variant pectate lyase according to claim 1 which has a degree of identity to the amino acid sequence of SEQ ID NO:2 of at least 97%.

6. A variant pectate lyase according to claim 1, wherein the variant has improved detergent stability compared to the parent enzyme.

7. A variant pectate lyase according to claim 1, wherein the alteration(s) is/are amino acid substitution(s).

8. A variant pectate lyase according to claim 1 comprising one or more substitutions selected from the group consisting of:

H5R, N11Y, K26Q, S28T, S30F, S30P, S30T, N37D, Q40E, L45V, G46D, K47N, K47R, T49P, N50D, N50L, N50Y, T51Y, T52M, K54V, T61A, M64F, D68*, N69*, L70*, K71*, K71E, G74D, L75A, L75P, N76D, K79A, D86N, K87A, K87E, A91E, K99I, K99N, K99R, T105A, T105P, E107K, A111E, K115A, K115I, K115N, K115Q, N116D, K118A, K118E, M122E, M122K, M122N, M122Q, V123I, S134L, T136S, K139E, K139F, K139I, K139M, K139N, K139S, V141G, V141E, V141L, V141N, Q146F, Q146H, Q146I, Q146V, K148E, K148Q, N156S, E158N, D170N, Q182D, Q182E, N185H, N186H, N189D, H193Y, I194V, I196V, C199N, C199S, F201L, N202K, G204R, K213E, K213N, K213T, K218E, K218L, K218P, G224S, A228I, S229T, Y234H, I235V, M237I, F251I, S256C, K257E, K257N, T258I, L256Y, R272C, R272H, R272Y, V277D, G286A, Y295H, 5298N, S301Y, S302A, S307R, Y308S, K314N, S316F, N323M, V324A, D326N, S331P, S331T, A332P, A333E, K334E, T335S, T335R, I336S, S337C, S337K, S337L, S337R, V338E, V338Y, F339I, S340A, S340K, S340N, S340P, S340Q, G341S, G349R, Q356H, I357V, N363S, S366N, A381D, H384N, K386P, K386R, S387A, V389I, I390N, I390T, A393V and K397D, and wherein each position corresponds to a position of the amino acid sequence of the pectate lyase having the amino acid sequence of SEQ ID NO:2.

9. The variant pectate lyase according to claim 8 which further comprises one or more substitutions selected from the group consisting of E9G, H31N, D48E, D48P, L106Q, I140V, F215Y, D303S, A305P, T378G, T378S, and S391N, wherein each position corresponds to a position of the amino acid sequence set forth in SEQ ID NO:2.

10. A cleaning comprising the variant as defined in claim 1 and further comprising a surfactant.

11. The composition according to claim 10 wherein the cleaning composition is a laundry detergent composition or a dish wash detergent composition.

12. A composition according to claim 10, which additionally comprises a cellulase, a lipase, a cutinase, an oxidoreductase, a protease, an amylase, a hemicellulase, such as a mannanase, a xylanase, a galactanase, an arabinofuranosidase, an esterase, a lichenase, an arabinanase, another pectate lyase or a mixture thereof.

* * * * *

```
                        SEQUENCE LISTING

<160> NUMBER OF SEQ ID NOS: 2

<210> SEQ ID NO 1
<211> LENGTH: 1200
<212> TYPE: DNA
<213> ORGANISM: Bacillus subtilis
<220> FEATURE:
<221> NAME/KEY: CDS
<222> LOCATION: (1)..(1200)

<400> SEQUENCE: 1 gct gat tta ggc cac cag acg tta gaa tca aat gat ggc tgg ggc gcg       48
Ala Asp Leu Gly His Gln Thr Leu Glu Ser Asn Asp Gly Trp Gly Ala
1               5                   10                  15 tac tcg acc ggc aca aca ggc gga tca aaa gct tcg tca tcc cac gtg       96
Tyr Ser Thr Gly Thr Thr Gly Gly Ser Lys Ala Ser Ser Ser His Val
            20                  25                  30 tat acc gtc agc aac aga aac cag ctt gtc tcg gca tta ggc aag gac      144
Tyr Thr Val Ser Asn Arg Asn Gln Leu Val Ser Ala Leu Gly Lys Asp
        35                  40                  45 acc aac aca acg cca aaa atc att tat att aag gga acg att gac atg      192
Thr Asn Thr Thr Pro Lys Ile Ile Tyr Ile Lys Gly Thr Ile Asp Met
    50                  55                  60 aac gtc gat gac aat ctg aag ccg ctt ggt cta aat gat tat aaa gat      240
Asn Val Asp Asp Asn Leu Lys Pro Leu Gly Leu Asn Asp Tyr Lys Asp
65                  70                  75                  80 cca gag tac gat ttg gac aaa tat ttg aaa gcc tat gac cct agc aca      288
Pro Glu Tyr Asp Leu Asp Lys Tyr Leu Lys Ala Tyr Asp Pro Ser Thr
                85                  90                  95 tgg ggc aaa aag gag ccg tcg ggg aca cta gaa gag gcg aga gca cga      336
Trp Gly Lys Lys Glu Pro Ser Gly Thr Leu Glu Glu Ala Arg Ala Arg
            100                 105                 110 tct cag aaa aat caa aaa gca cga gtc atg gtg gat att ccg gca aac      384
Ser Gln Lys Asn Gln Lys Ala Arg Val Met Val Asp Ile Pro Ala Asn
        115                 120                 125 acg acg atc gtc ggt tca ggg aca aat gcc aaa atc gtg ggc gga aat      432
Thr Thr Ile Val Gly Ser Gly Thr Asn Ala Lys Ile Val Gly Gly Asn
    130                 135                 140 ttc cag atc aag agt gat aat gtc atc atc cgc aac atc gaa ttc cag      480
Phe Gln Ile Lys Ser Asp Asn Val Ile Ile Arg Asn Ile Glu Phe Gln
145                 150                 155                 160 gat gct tat gat tat ttt ccg caa tgg gat ccg act gac ggc agc tca      528
Asp Ala Tyr Asp Tyr Phe Pro Gln Trp Asp Pro Thr Asp Gly Ser Ser
                165                 170                 175
```

-continued

```
gga aac tgg aac tca caa tac gac aac atc aca ata aac ggc ggc acg      576
Gly Asn Trp Asn Ser Gln Tyr Asp Asn Ile Thr Ile Asn Gly Gly Thr
            180                 185                 190 cat ata tgg att gat cat tgt aca ttt aat gac ggt tcc cgt ccg gac      624
His Ile Trp Ile Asp His Cys Thr Phe Asn Asp Gly Ser Arg Pro Asp
        195                 200                 205 agc aca tcg cca aag tat ttc ggc aga aaa tat cag cac cat gac ggc      672
Ser Thr Ser Pro Lys Tyr Phe Gly Arg Lys Tyr Gln His His Asp Gly
    210                 215                 220 caa acc gat gct tct aac ggc gct aac tat atc acg atg tct tac aac      720
Gln Thr Asp Ala Ser Asn Gly Ala Asn Tyr Ile Thr Met Ser Tyr Asn
225                 230                 235                 240 tat tat cac gat cat gat aaa agc tcc att ttc gga tca agc gac agc      768
Tyr Tyr His Asp His Asp Lys Ser Ser Ile Phe Gly Ser Ser Asp Ser
                245                 250                 255 aaa aca tct gat gac ggc aaa tta aaa atc acg ctc cat cat aac cgc      816
Lys Thr Ser Asp Asp Gly Lys Leu Lys Ile Thr Leu His His Asn Arg
            260                 265                 270 tat aaa aat atc gtc cag cgc gca ccg aga gtc cgc ttc ggg cag gtg      864
Tyr Lys Asn Ile Val Gln Arg Ala Pro Arg Val Arg Phe Gly Gln Val
        275                 280                 285 cac gtt tac aac aac tat tat gaa ggc agc aca agc tcc tcg gat tat      912
His Val Tyr Asn Asn Tyr Tyr Glu Gly Ser Thr Ser Ser Ser Asp Tyr
    290                 295                 300 gcc ttc agc tat gcg tgg gga atc gga aaa tca tct aaa atc tac gct      960
Ala Phe Ser Tyr Ala Trp Gly Ile Gly Lys Ser Ser Lys Ile Tyr Ala
305                 310                 315                 320 caa aac aat gtc att gac gtg cct gga ctg tca gcc gct aaa acg atc     1008
Gln Asn Asn Val Ile Asp Val Pro Gly Leu Ser Ala Ala Lys Thr Ile
                325                 330                 335 agc gta ttc agc ggg gga acg gct tta tat gac tca ggc aca ttg ctg     1056
Ser Val Phe Ser Gly Gly Thr Ala Leu Tyr Asp Ser Gly Thr Leu Leu
            340                 345                 350 aat ggc acg cag atc aac gca tcg gct gca aac ggg ctg agt tct tct     1104
Asn Gly Thr Gln Ile Asn Ala Ser Ala Ala Asn Gly Leu Ser Ser Ser
        355                 360                 365 gtc ggc tgg aca ccg tct ctg cac ggc aca atc gat gct tcc gcg cat     1152
Val Gly Trp Thr Pro Ser Leu His Gly Thr Ile Asp Ala Ser Ala His
    370                 375                 380 gta aaa tcg aat gtt ata tct caa gcg ggt gcg ggt aaa tta aat taa     1200
Val Lys Ser Asn Val Ile Ser Gln Ala Gly Ala Gly Lys Leu Asn
385                 390                 395
```

<210> SEQ ID NO 2
<211> LENGTH: 399
<212> TYPE: PRT
<213> ORGANISM: Bacillus subtilis

<400> SEQUENCE: 2

```
Ala Asp Leu Gly His Gln Thr Leu Glu Ser Asn Asp Gly Trp Gly Ala
1               5                   10                  15

Tyr Ser Thr Gly Thr Thr Gly Gly Ser Lys Ala Ser Ser His Val
            20                  25                  30

Tyr Thr Val Ser Asn Arg Asn Gln Leu Val Ser Ala Leu Gly Lys Asp
        35                  40                  45

Thr Asn Thr Thr Pro Lys Ile Ile Tyr Ile Lys Gly Thr Ile Asp Met
    50                  55                  60

Asn Val Asp Asp Asn Leu Lys Pro Leu Gly Leu Asn Asp Tyr Lys Asp
65                  70                  75                  80
```

```
Pro Glu Tyr Asp Leu Asp Lys Tyr Leu Lys Ala Tyr Asp Pro Ser Thr
            85              90              95

Trp Gly Lys Lys Glu Pro Ser Gly Thr Leu Glu Glu Ala Arg Ala Arg
            100             105             110

Ser Gln Lys Asn Gln Lys Ala Arg Val Met Val Asp Ile Pro Ala Asn
            115             120             125

Thr Thr Ile Val Gly Ser Gly Thr Asn Ala Lys Ile Val Gly Gly Asn
    130             135             140

Phe Gln Ile Lys Ser Asp Asn Val Ile Ile Arg Asn Ile Glu Phe Gln
145             150             155             160

Asp Ala Tyr Asp Tyr Phe Pro Gln Trp Asp Pro Thr Asp Gly Ser Ser
            165             170             175

Gly Asn Trp Asn Ser Gln Tyr Asp Asn Ile Thr Ile Asn Gly Gly Thr
            180             185             190

His Ile Trp Ile Asp His Cys Thr Phe Asn Asp Gly Ser Arg Pro Asp
            195             200             205

Ser Thr Ser Pro Lys Tyr Phe Gly Arg Lys Tyr Gln His His Asp Gly
    210             215             220

Gln Thr Asp Ala Ser Asn Gly Ala Asn Tyr Ile Thr Met Ser Tyr Asn
225             230             235             240

Tyr Tyr His Asp His Asp Lys Ser Ser Ile Phe Gly Ser Ser Asp Ser
            245             250             255

Lys Thr Ser Asp Asp Gly Lys Leu Lys Ile Thr Leu His His Asn Arg
            260             265             270

Tyr Lys Asn Ile Val Gln Arg Ala Pro Arg Val Arg Phe Gly Gln Val
            275             280             285

His Val Tyr Asn Asn Tyr Tyr Glu Gly Ser Thr Ser Ser Ser Asp Tyr
    290             295             300

Ala Phe Ser Tyr Ala Trp Gly Ile Gly Lys Ser Ser Lys Ile Tyr Ala
305             310             315             320

Gln Asn Asn Val Ile Asp Val Pro Gly Leu Ser Ala Ala Lys Thr Ile
            325             330             335

Ser Val Phe Ser Gly Gly Thr Ala Leu Tyr Asp Ser Gly Thr Leu Leu
            340             345             350

Asn Gly Thr Gln Ile Asn Ala Ser Ala Ala Asn Gly Leu Ser Ser Ser
            355             360             365

Val Gly Trp Thr Pro Ser Leu His Gly Thr Ile Asp Ala Ser Ala His
            370             375             380

Val Lys Ser Asn Val Ile Ser Gln Ala Gly Ala Gly Lys Leu Asn
385             390             395
```